United States Patent
De Kock et al.

(10) Patent No.: US 9,763,582 B2
(45) Date of Patent: *Sep. 19, 2017

(54) BARORECEPTOR MAPPING SYSTEM

(71) Applicant: Cardiac Pacemakers, Inc., St. Paul, MN (US)

(72) Inventors: Andrew L. De Kock, Andover, MN (US); Eric A. Mokelke, Flagstaff, AZ (US); Brian Soltis, St. Paul, MN (US); Doug E. Giwoyna, Harris, MN (US); James E. Blood, Shoreview, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 14/743,954

(22) Filed: Jun. 18, 2015

(65) Prior Publication Data
US 2015/0366465 A1 Dec. 24, 2015

Related U.S. Application Data

(60) Provisional application No. 62/014,390, filed on Jun. 19, 2014, provisional application No. 62/014,496, filed on Jun. 19, 2014.

(51) Int. Cl.
*A61B 5/021* (2006.01)
*A61B 5/0215* (2006.01)
(Continued)

(52) U.S. Cl.
CPC .............. *A61B 5/021* (2013.01); *A61B 5/024* (2013.01); *A61B 5/0215* (2013.01);
(Continued)

(58) Field of Classification Search
CPC ....... A61B 5/021; A61B 5/024; A61B 5/0531; A61B 5/6876
(Continued)

(56) References Cited

U.S. PATENT DOCUMENTS 5,476,493 A   12/1995   Muff
6,564,079 B1   5/2003   Cory et al.
(Continued)

FOREIGN PATENT DOCUMENTS

CN   101244315 A   8/2008
EP   2108398 B1   10/2009
(Continued)

OTHER PUBLICATIONS

International Preliminary Report on Patentability issued in PCT/US2014/046008, mailed Jan. 28, 2016, 8 pages.
(Continued)

*Primary Examiner* — Michael Carey
*Assistant Examiner* — Roland Dinga
(74) *Attorney, Agent, or Firm* — Faegre Baker Daniels LLP

(57) ABSTRACT

A system for mapping and marking baroreceptors of a patient. The system includes a mapping device, a marker, and a stimulator. The mapping device includes a plurality of electrodes to be situated on the patient. The marker is to be attached to the patient and mark a location of at least one of the plurality of electrodes based on an analysis of patient physiological responses to stimulation of the plurality of electrodes. The stimulator is to divide the plurality of electrodes into a first electrode zone and a second electrode zone and stimulate electrodes in the first electrode zone and the second electrode zone to obtain first patient physiological responses, where one of the first electrode zone and the second electrode zone is selected based on the first patient physiological responses.

9 Claims, 17 Drawing Sheets

(51) Int. Cl.
*A61B 5/024* (2006.01)
*A61B 5/053* (2006.01)
*A61B 5/00* (2006.01)
*A61N 1/04* (2006.01)
*A61N 1/05* (2006.01)
*A61N 1/36* (2006.01)
*A61B 5/02* (2006.01)
*A61B 90/00* (2016.01)

(52) U.S. Cl.
CPC ........ *A61B 5/02028* (2013.01); *A61B 5/0531* (2013.01); *A61B 5/4848* (2013.01); *A61B 5/6876* (2013.01); *A61B 90/39* (2016.02); *A61N 1/0476* (2013.01); *A61N 1/0556* (2013.01); *A61N 1/0558* (2013.01); *A61N 1/36117* (2013.01); *A61N 1/36185* (2013.01); *A61B 5/053* (2013.01); *A61B 2090/3908* (2016.02); *Y10T 156/1028* (2015.01)

(58) Field of Classification Search
USPC .......................................................... 607/62
See application file for complete search history.

(56) References Cited

U.S. PATENT DOCUMENTS

| | | | |
|---|---|---|---|
| 6,985,774 | B2 | 1/2006 | Kieval et al. |
| 7,015,061 | B2 | 3/2006 | Lu et al. |
| 7,337,005 | B2 | 2/2008 | Kim et al. |
| 7,445,953 | B2 | 11/2008 | Lu et al. |
| 7,502,650 | B2 | 3/2009 | Kieval |
| 7,616,997 | B2 | 11/2009 | Kieval et al. |
| 7,813,812 | B2 | 10/2010 | Kieval et al. |
| 8,126,560 | B2 | 2/2012 | Scheiner et al. |
| 8,175,705 | B2 | 5/2012 | Libbus |
| 8,571,664 | B2 | 10/2013 | Anderson et al. |
| 8,901,268 | B2 | 12/2014 | Krishnamoorthy et al. |
| 8,948,872 | B2 | 2/2015 | Shuros et al. |
| 9,345,877 | B2 | 5/2016 | Pignato et al. |
| 2002/0095080 | A1 | 7/2002 | Cory et al. |
| 2003/0187490 | A1 | 10/2003 | Gliner |
| 2004/0176759 | A1 | 9/2004 | Krishnamurthy et al. |
| 2005/0085884 | A1 | 4/2005 | O'Brien et al. |
| 2005/0096710 | A1 | 5/2005 | Kieval |
| 2005/0182456 | A1* | 8/2005 | Ziobro ................ A61B 5/0488 607/48 |
| 2006/0085049 | A1* | 4/2006 | Cory ................... A61B 5/0536 607/48 |
| 2006/0276704 | A1 | 12/2006 | McGinnis et al. |
| 2007/0021792 | A1 | 1/2007 | Kieval et al. |
| 2007/0027512 | A1 | 2/2007 | Chan et al. |
| 2007/0208391 | A1 | 9/2007 | Wahlstrand et al. |
| 2008/0004673 | A1 | 1/2008 | Rossing et al. |
| 2008/0046051 | A1 | 2/2008 | Skubitz et al. |
| 2008/0147146 | A1 | 6/2008 | Wahlgren et al. |
| 2009/0132002 | A1 | 5/2009 | Kieval |
| 2009/0143837 | A1 | 6/2009 | Rossing et al. |
| 2009/0234418 | A1 | 9/2009 | Kieval et al. |
| 2010/0152826 | A1 | 6/2010 | Tanabe et al. |
| 2010/0324641 | A1 | 12/2010 | Skubitz et al. |
| 2011/0257716 | A1 | 10/2011 | Tiedtke |
| 2013/0018247 | A1 | 1/2013 | Glenn et al. |
| 2015/0018918 | A1 | 1/2015 | Mokelke et al. |
| 2015/0165215 | A1 | 6/2015 | Mokelke et al. |
| 2015/0231391 | A1 | 8/2015 | Mokelke et al. |
| 2015/0366467 | A1 | 12/2015 | De Kock et al. |
| 2016/0059005 | A1 | 3/2016 | De Kock et al. |
| 2016/0074650 | A1 | 3/2016 | De Kock et al. |

FOREIGN PATENT DOCUMENTS

| | | |
|---|---|---|
| EP | 1487535 B1 | 6/2012 |
| JP | 2004526471 A | 9/2004 |
| JP | 2009532102 A2 | 9/2009 |
| JP | 2009532185 A | 9/2009 |
| JP | 2012130579 A | 7/2012 |
| KR | 20120053090 A | 5/2012 |
| WO | 0226314 A1 | 4/2002 |
| WO | 2007118090 A2 | 10/2007 |
| WO | 2015195980 A1 | 12/2015 |
| WO | 2015195982 A2 | 12/2015 |

OTHER PUBLICATIONS

International Search Report and Written Opinion issued in PCT/US2015/050303, mailed Jan. 14, 2016, 12 pages.
International Search Report and Written Opinion issued in PCT/US2015/036526, mailed Oct. 26, 2015, 12 pages.
International Search Report and Written Opinion Issued in PCT/US2015/036528, mailed Jan. 19, 2016, 15 pages.
International Search Report and Written Opinion] issued in PCT/US2014/046008, mailed Oct. 1, 2014, 12 pages.
Invitation to Pay Additional Fees and, Where Applicable, Protest Fee issued in PCT/US2015/036528, mailed Oct. 28, 2015, 6 pages.
International Preliminary Report on Patentability issued in PCT/US2015/036526, issued on Dec. 20, 2016, 8 pages.
International Preliminary Report on Patentability issued in PCT/US2015/036528, issued on Dec. 20, 2016, 9 pages.
International Preliminary Report on Patentability issued in PCT/US2015050303, dated Mar. 30, 2017, 8 pages.

* cited by examiner

BARORECEPTOR MAPPING SYSTEM

CROSS-REFERENCE TO RELATED APPLICATION

This application claims priority to Provisional Application No. 62/014,390, filed Jun. 19, 2014, and to Provisional Application No. 62/014,496, filed Jun. 19, 2014, both of which are herein incorporated by reference in their entirety.

TECHNICAL FIELD

This disclosure relates generally to medical devices, and more particularly, to systems, devices, and methods for delivering electrical stimulation.

BACKGROUND

Neural stimulation has been proposed as a therapy to treat hypertension, also referred to as high blood pressure. It has been proposed that electrical stimulation directed at baroreceptor regions can be used to induce a baroreceptor reflex (baroreflex) that reduces blood pressure. Through the negative feedback loop of the baroreflex, the central nervous system regulates the blood pressure to maintain the blood pressure at a relatively stable level. For example, high blood pressure that causes arterial stretching activates baroreceptors to send nerve impulses to the brain and, in response, the brain controls the pumping activity of the heart and blood vessel dilation to reduce the blood pressure.

The change in the blood pressure that is due to electrical stimulation of a site in a baroreceptor region fluctuates dramatically based on the location of the site in the baroreceptor region, i.e., the change in the blood pressure due to the stimulation at a first site in the baroreceptor region can be significantly different than the change in the blood pressure due to the stimulation at a second site in the baroreceptor region. Animal experiments indicate that stimulation sites separated by less than 1 millimeter (mm) can produce dramatically different changes in the blood pressure. Thus, the implantation of a stimulation device on a baroreceptor region usually requires extensive mapping of the region to find a location that provides effective or the most effective control of the blood pressure.

Often, surgeons manually hold one or more electrodes at various locations on the baroreceptor region to map the region during an implantation procedure. Mapping the baroreceptor region takes significant time and effort due to the difficulty of manually positioning the electrode at a site, stimulating the baroreceptor region at the site, waiting for the change in the blood pressure, measuring the change in the blood pressure, and letting the blood pressure return to a steady level before positioning the electrode at the next site and repeating the process. Longer procedure times increase the risk to a patient and lead to physician fatigue and dissatisfaction. In addition, this manual procedure can introduce mechanical activation of the baroreceptors, which hinders the evaluation of the change in the blood pressure that is due to the electrical stimulation. As a result, full mapping of the baroreceptor region is often not obtained, which can result in sub-optimal implant location, sub-optimal stimulation therapy, and, over time, loss of therapeutic value.

SUMMARY

Example 1 is a system for mapping and marking baroreceptors of a patient. The system includes a mapping device, a marker, and a stimulator. The mapping device includes a plurality of electrodes to be situated on the patient. The marker is to be attached to the patient and mark a location of at least one of the plurality of electrodes based on an analysis of patient physiological responses to stimulation of the plurality of electrodes. The stimulator is to divide the plurality of electrodes into a first electrode zone and a second electrode zone and stimulate electrodes in the first electrode zone and the second electrode zone to obtain first patient physiological responses, where one of the first electrode zone and the second electrode zone is selected based on the first patient physiological responses.

In Example 2, the system of Example 1 where the stimulator is to divide the selected one of the first electrode zone and the second electrode zone into a third electrode zone and a fourth electrode zone and to stimulate electrodes in the third electrode zone and the fourth electrode zone to obtain second patient physiological responses, where one of the third electrode zone and the fourth electrode zone is selected based on the second patient physiological responses.

In Example 3, the system of any of Examples 1 and 2, where the stimulator is to divide the selected one of the third electrode zone and the fourth electrode zone into a fifth electrode zone and a sixth electrode zone and to stimulate electrodes in the fifth electrode zone and the sixth electrode zone to obtain third patient physiological responses, where one of the fifth electrode zone and the sixth electrode zone is selected based on the third patient physiological responses.

In Example 4, the system of any of Examples 1-3, where the stimulator selects the at least one of the plurality of electrodes to be marked by the marker.

In Example 5, the system of any of Examples 1-4, where a user selects the at least one of the plurality of electrodes to be marked by the marker.

In Example 6, the system of any of Examples 1-5, where the stimulator is to select at least one cathode electrode in the first electrode zone and at least one anode electrode in the second electrode zone and provide bipolar stimulation to the selected electrodes to obtain the first patient physiological responses.

In Example 7, the system of any of Examples 1-6, where the stimulator switches to selecting the at least one cathode electrode in the second electrode zone and the at least one anode electrode in the first electrode zone and provides bipolar stimulation to the selected electrodes to obtain the first patient physiological responses.

In Example 8, the system of any of Examples 1-7, where the stimulator selects the one of the first electrode zone and the second electrode zone based on the first patient physiological responses.

In Example 9, the system of any of Examples 1-8, comprising a sensor to sense the patient physiological responses and provide signals that indicate the patient physiological responses, where the stimulator receives the signals and analyzes the signals to determine the first patient physiological responses.

Example 10 is a method of mapping and marking baroreceptors of a patient including: maintaining a mapping device on the patient, the mapping device including a plurality of electrodes; dividing the plurality of electrodes, via a stimulator, into a first electrode zone and a second electrode zone; stimulating electrodes in the first electrode zone and the second electrode zone, via the stimulator, to obtain patient physiological responses; and selecting one of the first electrode zone and the second electrode zone based on the patient physiological responses for attaching a marker to the patient to mark a location of at least one of the plurality of electrodes based on the patient physiological responses.

In Example 11, the method of Example 10 including: dividing the selected one of the first electrode zone and the second electrode zone, via the stimulator, into a third electrode zone and a fourth electrode zone; stimulating electrodes in the third electrode zone and the fourth electrode zone, via the stimulator, to obtain more patient physiological responses; and selecting one of the third electrode zone and the fourth electrode zone based on the patient physiological responses including the more patient physiological responses.

In Example 12, the method of any of Examples 10 and 11 including: selecting at least one cathode electrode in the first electrode zone; selecting at least one anode electrode in the second electrode zone; and providing bipolar stimulation, via the stimulator, to the selected electrodes to obtain the patient physiological responses.

In Example 13, the method of any of Examples 10-12 including: switching to selecting the at least one cathode electrode in the second electrode zone; switching to selecting the at least one anode electrode in the first electrode zone; and providing bipolar stimulation, via the stimulator, to the selected electrodes to obtain the patient physiological responses.

In Example 14, the method of any of Examples 10-13 including: selecting, via the stimulator, the one of the first electrode zone and the second electrode zone based on the patient physiological responses.

In Example 15, the method of any of Examples 10-14 including: sensing the patient physiological responses with a sensor; providing signals that indicate the patient physiological responses; receiving the signals at the stimulator; and analyzing the signals with the stimulator to determine the one of the first electrode zone and the second electrode zone that is selected based on the patient physiological responses.

Example 16 is a system for mapping and marking baroreceptors of a patient. The system includes a mapping device and a stimulator. The mapping device includes a plurality of electrodes to be situated on the patient. The stimulator is to divide the plurality of electrodes into a first electrode zone and a second electrode zone and to stimulate electrodes in the first electrode zone and in the second electrode zone to obtain patient physiological responses. One of the first electrode zone and the second electrode zone is selected based on the patient physiological responses.

In Example 17, the system of Example 16, where the stimulator is to divide the selected one of the first electrode zone and the second electrode zone into a third electrode zone and a fourth electrode zone and to stimulate electrodes in the third electrode zone and the fourth electrode zone to obtain the patient physiological responses.

In Example 18, the system of any of Examples 16 and 17, where one of the third electrode zone and the fourth electrode zone is selected as providing more effective patient physiological responses.

In Example 19, the system of any of Examples 16-18, where the stimulator is to select at least one cathode electrode in the first electrode zone and at least one anode electrode in the second electrode zone and provide electrical stimulation to the selected electrodes to obtain first patient physiological responses.

In Example 20, the system of any of Examples 16-19, where the stimulator switches to select the at least one cathode electrode in the second electrode zone and the at least one anode electrode in the first electrode zone and provide electrical stimulation to the selected electrodes to obtain second patient physiological responses.

In Example 21, the system of any of Examples 16-20, where the stimulator compares the first patient physiological responses and the second patient physiological responses to select the one of the first electrode zone and the second electrode zone.

In Example 22, the system of any of Examples 16-21, including a marker to be attached to the patient to mark a location of at least one of the plurality of electrodes based on the patient physiological responses.

In Example 23, the system of any of Examples 16-22, where the patient physiological responses are changes in one of patient blood pressure, patient heart rate, and patient tissue impedance.

In Example 24, the system of any of Examples 16-23, including a sensor to sense the patient physiological responses and provide signals that indicate the patient physiological responses.

In Example 25, the system of any of Examples 16-24, where the stimulator receives the signals and analyzes the signals to determine the patient physiological responses and the one of the first electrode zone and the second electrode zone that is selected based on the patient physiological responses.

Example 26 is a method of mapping and marking baroreceptors, which includes: maintaining a mapping device on a patient, the mapping device including a plurality of electrodes on the patient; dividing the plurality of electrodes, via a stimulator, into a first electrode zone and a second electrode zone; stimulating electrodes in the first electrode zone and the second electrode zone with the stimulator to obtain patient physiological responses; and selecting one of the first electrode zone and the second electrode zone based on the patient physiological responses.

In Example 27, the method of Example 26 including: dividing the selected one of the first electrode zone and the second electrode zone, via the stimulator, into a third electrode zone and a fourth electrode zone; and stimulating electrodes in the third electrode zone and the fourth electrode zone with the stimulator to obtain more patient physiological responses.

In Example 28, the method of any of Examples 26 and 27 including selecting one of the third electrode zone and the fourth electrode zone based on the patient physiological responses including the more patient physiological response.

In Example 29, the method of any of Examples 26-28 including attaching a marker to the patient to mark a location of at least one of the plurality of electrodes based on an analysis of the patient physiological responses.

In Example 30, the method of any of Examples 26-29 where stimulating electrodes in the first electrode zone and the second electrode zone includes: selecting at least one cathode electrode in the first electrode zone; selecting at least one anode electrode in the second electrode zone; and stimulating, via the stimulator, the selected electrodes to obtain the patient physiological responses.

In Example 31, the method of any of Examples 26-30 where stimulating electrodes in the first electrode zone and the second electrode zone includes: selecting at least one cathode electrode in the second electrode zone; selecting at least one anode electrode in the first electrode zone; and stimulating, via the stimulator, the selected electrodes to obtain the patient physiological responses.

In Example 32, the method of any of Examples 26-31, including: sensing the patient physiological responses with a sensor; providing signals that indicate the patient physiological responses; receiving the signals at the stimulator; and analyzing the signals with the stimulator to determine the one of the first electrode zone and the second electrode zone that is selected based on the patient physiological responses.

Example 33 includes one or more non-transitory computer-readable storage media having computer-executable instructions embodied thereon that, when executed by a processor, cause the processor to provide a method including: dividing a plurality of electrodes on a mapping device into a first electrode zone and a second electrode zone; selecting at least one cathode electrode in the first electrode zone; selecting at least one anode electrode in the second electrode zone; stimulating the at least one cathode electrode in the first electrode zone and the at least one anode electrode in the second electrode zone to obtain first patient physiological responses; selecting at least one cathode electrode in the second electrode zone; selecting at least one anode electrode in the first electrode zone; stimulating the at least one cathode electrode in the second electrode zone and the at least one anode electrode in the first electrode zone to obtain second patient physiological responses; and comparing the first patient physiological responses and the second patient physiological responses to select one of the first electrode zone and the second electrode zone.

In Example 34, the media of Example 33, where the method includes: dividing the selected one of the first electrode zone and the second electrode zone into a third electrode zone and a fourth electrode zone; selecting at least one cathode electrode in the third electrode zone; selecting at least one anode electrode in the fourth electrode zone; stimulating the at least one cathode electrode in the third electrode zone and the at least one anode electrode in the fourth electrode zone to obtain third patient physiological responses; selecting at least one cathode electrode in the fourth electrode zone; selecting at least one anode electrode in the third electrode zone; stimulating the at least one cathode electrode in the fourth electrode zone and the at least one anode electrode in the third electrode zone to obtain fourth patient physiological responses; and comparing the third patient physiological responses and the fourth patient physiological responses to select one of the third electrode zone and the fourth electrode zone.

In Example 35, the media of any of Examples 33 and 34, where the method includes: receiving signals from a sensor; and analyzing the signals to determine the first physiological responses and the second physiological responses.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
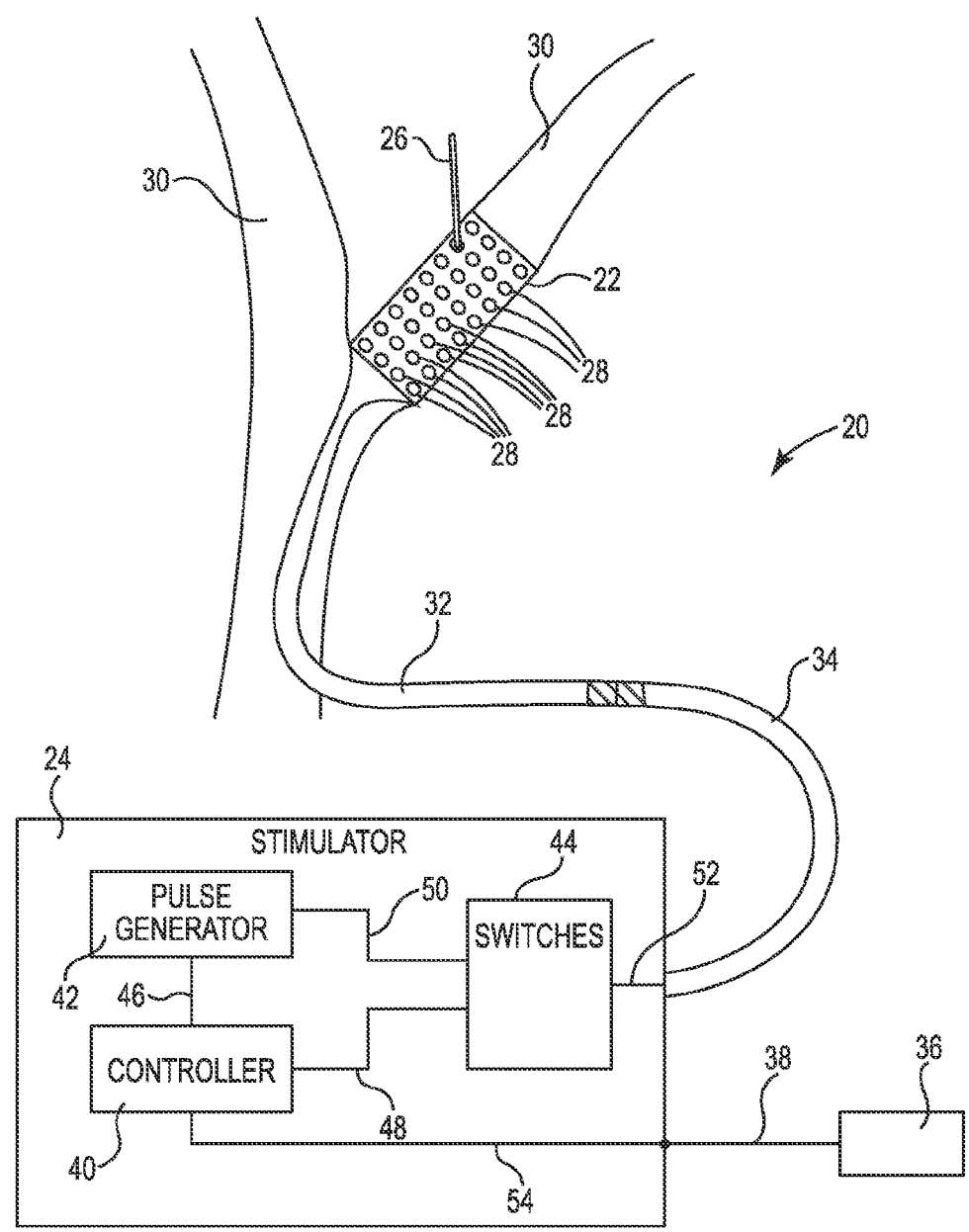
FIG. 1 is a diagram illustrating a system for mapping and marking baroreceptors in a baroreceptor region of a patient, according to some embodiments described in the disclosure.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Disclosed herein are systems, devices, and methods for: mapping a baroreceptor region using a mapping device; marking a location on the baroreceptor region based on the mapping results; and positioning an implantable device at the location on the baroreceptor region after removing the mapping device from the baroreceptor region.

The autonomic nervous system (ANS) regulates involuntary organs, such as respiratory organs, digestive organs, blood vessels, and the heart. The ANS can function in an involuntary, reflexive manner to regulate glands and muscles in the skin, eye, stomach, intestines and bladder, and to regulate cardiac muscle and the muscles around blood vessels. The ANS includes the sympathetic nervous system and the parasympathetic nervous system. The sympathetic nervous system is related to stress and the "fight or flight response." Among other effects, the "fight or flight response" increases blood pressure and heart rate to increase skeletal muscle blood flow, and it decreases digestion to provide energy for fighting or fleeing. The parasympathetic nervous system is related to relaxation and the "rest and digest response" which, among other effects, decreases blood pressure and heart rate and increases digestion. The heart rate and force are increased when the sympathetic nervous system is stimulated and decreased when the sympathetic nervous system is inhibited and the parasympathetic nervous system is stimulated.

A pressoreceptive region, also referred to as a baroreceptor region, senses changes in pressure, such as changes in blood pressure. Baroreceptors in the baroreceptor region are sensitive to the stretching of a blood vessel wall that is due to an increase in the blood pressure. The baroreceptors function as the receptor of the central reflex mechanism referred to as the baroreflex. Activated baroreceptors trigger the baroreflex that functions as a negative feedback loop to reduce the blood pressure. In operation of the baroreflex, an increase in the blood pressure stretches the blood vessels, which in turn activates the baroreceptors in the blood vessel wall. Activation of the baroreceptors inhibits the sympathetic nervous system and excites the parasympathetic nervous system, which decreases peripheral vascular resistance and decreases cardiac rate and contractility to reduce the blood pressure.

Baroreceptors can be electrically stimulated to induce the baroreflex, where, as used herein, electrical stimulation of a baroreceptor includes stimulating the nerve tissue including the nerve endings that innervate the baroreceptors. Stimulation of the nerve tissue near the baroreceptors causes neural signals to be sent to the central nervous system and induces the baroreflex. The electrical stimulation of the baroreceptors to induce the baroreflex has been proposed for various therapies, including hypertension therapy, heart failure therapy, and arrhythmia therapy. The electrical stimulation of the baroreceptors can be unipolar or bipolar stimulation. However, modeling suggests that it is the tissue directly under a cathode that receives the greatest amount of energy, such that cathodes can be situated in the baroreceptor region for mapping the baroreceptor region and the location of the anode, which appears to be less significant, can be positioned away from the baroreceptor region.

Baroreceptors are located throughout the body, including in the arch of the aorta and the carotid sinuses of the left and right internal carotid arteries. Baroreceptor distribution may vary from person-to-person. However, baroreceptors appear to be more highly concentrated near the bifurcation of the interior carotid artery (ICA) and external carotid artery (ECA), off of the common carotid artery (CCA).

FIG. 1 is a diagram illustrating a system 20 for mapping and marking baroreceptors in a baroreceptor region of a patient, according to some embodiments described in the disclosure. The system 20 includes a mapping device 22, a stimulator 24, and a marker 26. The system 20 can be used to map and mark the baroreceptors in a baroreceptor region, such as the carotid sinus of the ICA, the carotid sinus of the ECA, the area near the bifurcation of the ICA and the ECA, the arch of the aorta artery, and others.

The mapping device 22 includes a plurality of mapping electrodes 28 to be situated on the baroreceptor region. The mapping electrodes 28 are used to deliver electrical stimulation to the baroreceptor region. The mapping device 22 is shaped to fit onto the baroreceptor region and hold the mapping electrodes 28 on the baroreceptor region. In FIG. 1, the mapping device 22 is rectangular shaped and situated on an artery 30. In some embodiments, the mapping device 22 is configured to wrap fully around the artery 30 and hold the mapping electrodes 28 in place on the baroreceptor region. In some embodiments, the mapping device 22 is configured to wrap partially around the artery 30 and hold the mapping electrodes 28 in place on the baroreceptor region. In some embodiments, the mapping device 22 is configured to be pressed against the artery 30 and hold the mapping electrodes 28 in place on the baroreceptor region. In some embodiments, the mapping device 22 is configured to hold the mapping electrodes 28 in place on the baroreceptor region, wherever the baroreceptor region may be on the patient's body.

The mapping device 22, including the plurality of mapping electrodes 28, is electrically coupled to the stimulator 24 by a mapping device cable 32 and a re-usable connector cable 34. In some embodiments, each of the mapping electrodes 28 is electrically coupled to a separate lead in the cable 32 and each of the separate leads is electrically coupled to the stimulator 24 through the re-usable connector cable 34. In some embodiments, the cable 32 is electrically coupled directly to the stimulator 24.

The stimulator 24 selects one or more of the mapping electrodes 28 and stimulates the selected mapping electrode(s) to obtain one or more physiological responses from the patient. In some embodiments, the stimulator 24 can deliver unipolar or bipolar electrical stimulation to the tissue of the baroreceptor region through the mapping electrodes 28. In some embodiments, the one or more physiological responses includes a change in the patient's blood pressure. In some embodiments, the one or more physiological responses includes a change in the patient's heart rate. In some embodiments, the one or more physiological responses includes a change in the patient's tissue impedance.

The physiological responses can be obtained manually from the patient or, at least optionally, in some embodiments, the physiological responses can be obtained automatically from the patient using one or more sensors, such as sensor 36. The sensor 36 is in communication with the patient or attached to the patient and communicatively coupled to the stimulator 24 via communications path 38. The sensor 36 senses at least one physiological parameter under consideration and provides signals that indicate the sensed physiological parameter. The at least one physiological parameter under consideration can include the patient's blood pressure, the patient's heart rate, and the patient's tissue impedance. In some embodiments, the sensor 36 can include a direct pressure sensor. In some embodiments, the sensor 36 can include a heart rate sensor. In some embodiments, the sensor 36 can include a tissue impedance sensor.

The stimulator 24 receives the signals from the sensor 36, analyzes the signals to obtain the physiological responses, and stores the data in a map of the baroreceptor region, indicating the electrode(s) stimulated and the corresponding physiological responses. This process is repeated for at least some of the plurality of mapping electrodes 28 to map the baroreceptor region.

The map of the baroreceptor region is analyzed to obtain the location of at least one of the mapping electrodes 28 that, when stimulated, provides an effective physiological response, referred to herein as the identified effective location on the baroreceptor region. The effective physiological response can be a level of change that matches or exceeds a threshold level of change in one or more of the physiological parameters under consideration. In some embodiments, the stimulator 24 analyzes the map of the baroreceptor region to obtain the location on the baroreceptor region of the at least one of the mapping electrodes 28 that provides the effective physiological response.

In one example, the stimulator 24 selects one of the mapping electrodes 28 and, to stimulate the patient, the stimulator 24 provides electrical current through the selected mapping electrode 28. The patient's blood pressure changes in response to the electrical current through the selected mapping electrode 28, where the change in the patient's blood pressure begins after the electrical stimulation has begun and is usually complete within 1 minute from the beginning of the electrical stimulation. In some embodiments, the stimulator 24 provides between 2 and 5 milliamps (mA) of electrical current through the mapping electrode 28 to stimulate the patient. In some embodiments, the stimulator 24 provides between 2.9 and 4.1 mA of electrical current through the mapping electrode 28 to stimulate the patient. In some embodiments, the stimulator 24 provides the electrical current over a period of less than 5 seconds. In some embodiments, the patient's blood pressure begins changing within 5 seconds of the beginning of the electrical stimulation and the measurement of the change in blood pressure ends 1 minute or less after the stimulation has begun.

To further this example, the sensor 36 includes a pressure sensor that provides signals that indicate the patient's blood pressure. The stimulator 24 receives the signals and analyzes the signals to obtain the change in the patient's blood pressure. The stimulator 24 stores the data in a map of the baroreceptor region, indicating the electrode stimulated and the corresponding change in blood pressure. This process is repeated for at least one other electrode of the plurality of mapping electrodes 28 to map the baroreceptor region. The stimulator 24 analyzes the map of the baroreceptor region to select the location in the baroreceptor region that provides the largest reduction in the patient's blood pressure within 1 minute, which in this example is the effective physiological response. To analyze the map and select the location, the stimulator 24 compares the magnitudes of the change in blood pressure for different electrode locations and selects the largest change in blood pressure, which is a reduction in blood pressure, and the corresponding electrode location. In some embodiments, the reduction in blood pressure may be greater than 10 mmHg in response to a 3 mA stimulation through one of the electrodes.

In some embodiments, the stimulator 24 includes a stimulation controller 40, a stimulation pulse generator 42, and switches 44. The controller 40 is communicatively coupled to the pulse generator 42 via communications path 46 and to the switches 44 via communications path 48. The pulse generator 42 is electrically coupled to the switches 44 via conductive path 50 and the switches 44 are electrically coupled to the re-usable connector cable 34, the cable 32, and the plurality of mapping electrodes 28 via conductive path 52. In some embodiments, the controller 40 is communicatively coupled to the sensor 36 via communications paths 38 and 54.

The controller 40 executes computer-executable instructions that cause the stimulator 24 to provide the system and methods described in this disclosure. In some embodiments, the controller 40 is at least one processor. In some embodiments, the stimulator 24 includes memory including one or more non-transitory computer-readable storage media having computer-executable instructions embodied thereon that, when executed by the controller 40, cause the stimulator 24 to provide the system and methods described in this disclosure.

The controller 40 controls the switches 44 to selectively connect one or more of the mapping electrodes 28 to the pulse generator 42. In some embodiments, the controller 40 controls the switches 44 to connect one or more of the mapping electrodes 28 to the pulse generator 42 as one or more cathodes. In some embodiments, the controller 40 controls the switches 44 to connect one or more of the mapping electrodes 28 to the pulse generator 42 as one or more anodes.

The controller 40 controls the pulse generator 42 to stimulate the connected mapping electrodes 28. In some embodiments, the pulse generator 42 can provide unipolar or bipolar electrical stimulation to the tissue of the baroreceptor region through the mapping electrodes 28. In some embodiments, the controller 40 controls the switches 44 to connect two or more of the mapping electrodes 28 to the pulse generator 42 for bipolar stimulation, i.e., at least one cathode electrode and at least one anode electrode. In some embodiments, the controller 40 controls the switches 44 to connect one or more of the mapping electrodes 28 to the pulse generator 42 for unipolar stimulation.

In some embodiments, the controller 40 receives the signals from the sensor 36 and analyzes the signals to obtain the physiological responses from the patient. The controller 40 stores the data in a map of the baroreceptor region, indicating the electrode(s) stimulated and the corresponding physiological response. In some embodiments, the controller 40 analyzes the map of the baroreceptor region to obtain the location of at least one of the mapping electrodes 28 that, when stimulated, provides an effective physiological response, referred to herein as the identified effective location in the baroreceptor region.

The marker 26 is to be attached to the patient to mark the location in the baroreceptor region of at least one of the mapping electrodes 28 based on an analysis of the physiological responses from the patient. The marker 26 can be attached to the patient after the mapping device 22 and the stimulator 24 have mapped the baroreceptor region and the map has been analyzed to identify an electrode location that, when stimulated, provides an effective physiological response. The marker 26 is attached to the patient relative to the identified electrode location to indicate and keep track of the identified effective location on the baroreceptor region. The marker 26 maintains its location on the patient while the mapping device 22 is removed from the patient and after the mapping device 22 has been removed from the patient.

An implantable device (not shown in FIG. 1), including an implantable electrode, is aligned on the baroreceptor region using the marker 26, where the implantable electrode is situated on the identified effective location. The implantable device is sutured into place on the baroreceptor region and the implantable electrode is used to stimulate the baroreceptors at the identified effective location to alleviate hypertension. After the implantable device is attached to the patient, the marker 26 is removed from the patient. In some embodiments, multiple markers can be used to keep track of the identified effective location on the baroreceptor region. In some embodiments, the marker 26 includes a pin. In some embodiments, the marker 26 includes a thread sutured into place.

In one example, the controller 40 controls the switches 44 to selectively connect two of the mapping electrodes 28 to the pulse generator 42. The controller 40 controls the switches 44 to connect one of the mapping electrodes 28 to the pulse generator 42 as a cathode and the other of the mapping electrodes 28 to the pulse generator 42 as an anode. The controller 40 controls the pulse generator 42 to stimulate the connected mapping electrodes 28, providing bipolar electrical stimulation to the tissue of the baroreceptor region through the mapping electrodes 28. The patient provides a physiological response, such as a change in blood pressure and a change in heart rate, primarily in response to the stimulation of the tissue under the cathode. In some embodiments, the pulse generator 42 provides between 2 and 5 milliamps (mA) of electrical current through the mapping electrodes 28 to stimulate the patient. In some embodiments, the pulse generator 42 provides between 2.9 and 4.1 mA of electrical current through the mapping electrodes 28 to stimulate the patient. In some embodiments, the pulse generator 42 provides the electrical current over a period of less than 5 seconds. In some embodiments, the patient's blood pressure and heart rate begin to change within 5 seconds of the beginning of the electrical stimulation and the measurement of the changes end 1 minute or less after the stimulation has begun.

To further this example, the controller 40 receives signals from the sensor 36 indicating the patient's blood pressure and heart rate, and the controller 40 analyzes the signals to obtain the reductions in the patient's blood pressure and heart rate. The controller 40 stores the data in a map of the baroreceptor region, indicating the cathode electrode stimulated and the corresponding physiological responses. To analyze the map of the baroreceptor region, the controller 40 compares the magnitudes of the reductions in the blood pressure and the heart rate at one cathode electrode to the reductions at another cathode electrode. The controller 40 selects the cathode electrode providing the largest changes to obtain the location of the one mapping electrode 28 that, when stimulated, provides the effective physiological response. In some embodiments, the controller 40 can include a tie breaking scheme, such as selecting a cathode electrode providing the largest reduction in blood pressure over a cathode electrode providing the largest reduction in heart rate.

In addition, in this example, the marker 26 is attached to the patient to mark the location of the selected mapping electrode 28 and to keep track of the identified effective location on the baroreceptor region. The marker 26 maintains its location on the patient while the mapping device 22 is removed from the patient and after the mapping device 22 has been removed from the patient. Next, an implantable device including an implantable electrode is aligned on the baroreceptor region using the marker 26, where the implantable electrode is situated on the identified effective location. The implantable device is sutured into place on the baroreceptor region and the implantable electrode is used to stimulate the baroreceptors at the identified effective location to alleviate hypertension. After the implantable device is attached to the patient, the marker 26 is removed from the patient.

Figure 2:
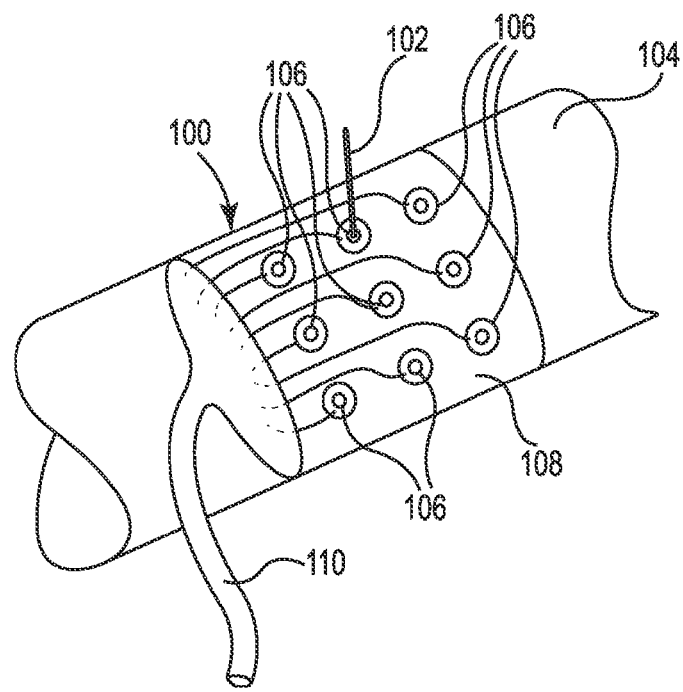
FIG. 2 is a diagram illustrating a mapping device and a marker situated on an artery, according to some embodiments described in the disclosure.

FIG. 2 is a diagram illustrating a mapping device 100 and a marker 102 situated on an artery 104, according to some embodiments described in the disclosure. The mapping device 100 and the marker 102 can be attached to the artery 104. In some embodiments, the mapping device 100 is similar to the mapping device 22 (shown in FIG. 1). In some embodiments, the marker 102 is similar to the marker 26 (shown in FIG. 1).

The mapping device 100 can be attached to the artery 104 to map a baroreceptor region of the artery 104. The mapping device 100 has a first side facing the artery 104 and a second side that opposes the first side and faces away from the artery 104. In some embodiments, the mapping device 100 is curled or wrapped around the artery 104 to hold the mapping device 100 in place on the artery 104. In some embodiments, the mapping device 100 includes a self-curling sheet that curls the mapping device 100 around the artery 104 and fixes the mapping device 100 to the baroreceptor region. In some embodiments, the backing of the mapping device 100 is formed to curl the mapping device 100 around the artery 104 and fix the mapping device 100 to the baroreceptor region.

The mapping device 100 includes a plurality of mapping electrodes 106 formed on a substrate 108. The mapping electrodes 106 can be arranged in an array of mapping electrodes 106. The substrate 108 includes at least one insulating layer on the first side of the mapping device 100 and the mapping electrodes 106 are formed on the insulating layer of the substrate 108. The mapping electrodes 106 are situated on the first side of the substrate 108 to face the artery 104 and contact the tissue of the baroreceptor region. In some embodiments, the substrate 108 is formed to curl the mapping device 100 around the artery 104 and fix the mapping device 100 to the baroreceptor region. In some embodiments, the mapping device 100 is configured to wrap fully around the artery 104 and hold the mapping electrodes 106 in place on the baroreceptor region. In some embodiments, the mapping device 100 is configured to wrap partially around the artery 104 and hold the mapping electrodes 106 in place on the baroreceptor region. In some embodiments, the mapping device 100 is configured to be pressed against the artery 104 and hold the mapping electrodes 106 in place on the baroreceptor region.

The mapping electrodes 106 are made out of a conductive material and electrically coupled to a mapping device cable 110, which is electrically coupled to a stimulator, such as stimulator 24 (shown in FIG. 1). In some embodiments, the mapping electrodes 106 include metal. In some embodiments, the mapping electrodes 106 include copper. In some embodiments, each of the mapping electrodes 106 is electrically isolated from the other mapping electrodes 106 on the substrate 108. In some embodiments, the mapping device 100 is built using printed circuit board technology.

The marker 102 is attached to the artery 104 to indicate and keep track of the identified effective location in the baroreceptor region for stimulating the baroreceptor region and obtaining the desired physiological response from the patient. The marker 102 is attached to the artery 104 relative to the mapping device 100. In some embodiments, multiple markers, such as marker 102, can be attached to the artery 104 relative to the mapping device 100 to indicate and keep track of the identified effective location in the baroreceptor region.

The marker 102 can be attached to the tissue of the artery 104 through a marking aperture in the mapping device 100 or at one or more locations next to the mapping device 100. The marking aperture can be a through-hole aperture in the mapping device 100, which extends completely through the mapping device 100, from the first side of the mapping device 100 to the second side of the mapping device 100. In some embodiments, the mapping device 100 includes a through-hole aperture through each of the plurality of mapping electrodes 106 and the marker 102 is attached to the artery 104 through one of these through-hole apertures. In some embodiments, the mapping device 100 includes a through-hole aperture next to each of the plurality of electrodes 106 and the marker 102 is attached to the artery 104 through one of these through-hole apertures. In some embodiments, the mapping device 100 includes one or more through-hole apertures at the periphery of the mapping device 100, outside the plurality of mapping electrodes 106, and one or more markers, such as marker 102, are attached to the artery 104 through these through-hole apertures.

Figure 3:
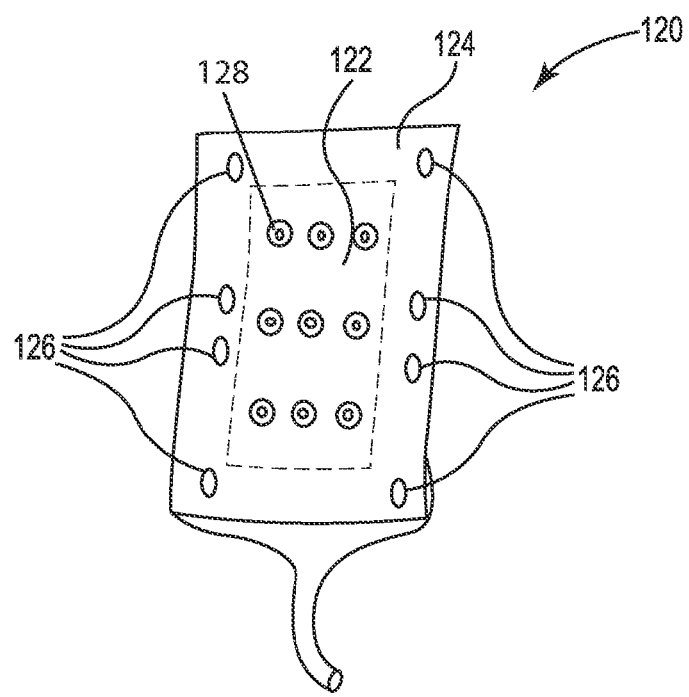
FIG. 3 is a diagram illustrating a mapping device including a mapping electrode region and a periphery region, according to some embodiments described in the disclosure.

FIG. 3 is a diagram illustrating a mapping device 120 including a mapping electrode region 122 and a periphery region 124 that is outside the mapping electrode region 122 as indicated by dashed lines, according to some embodiments described in the disclosure. In some embodiments, the mapping device 120 is similar to the mapping device 100.

The mapping electrode region 122 includes mapping electrodes 128 and the periphery region 124 includes through-hole apertures 126 that extend through the mapping device 120. Markers, such as marker 102, can be attached to the tissue of the baroreceptor region through the through-hole apertures 126 in the periphery region 124 to indicate and keep track of the identified effective location in the baroreceptor region. In some embodiments, the mapping electrodes 128 are similar to the mapping electrodes 106.

Figure 4:
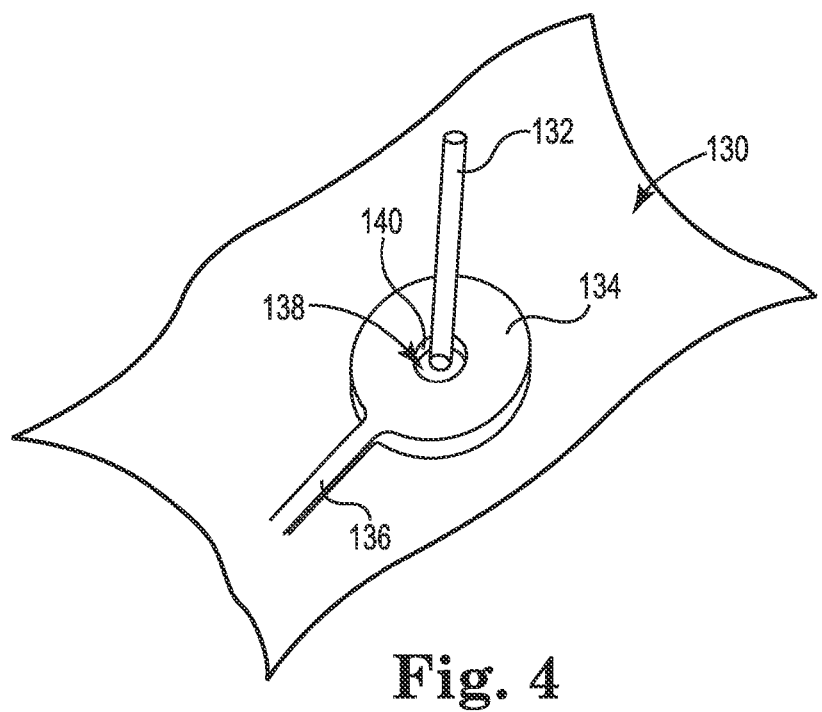
FIG. 4 is a diagram illustrating a mapping device and a marker, where the mapping device includes a through-hole aperture through a mapping electrode, according to some embodiments described in the disclosure.

FIG. 4 is a diagram illustrating a mapping device 130 and a marker 132, according to some embodiments described in the disclosure. The mapping device 130 includes a mapping electrode 134 that is made from a conductive material and includes a conductive lead 136 that can be electrically coupled to a mapping device cable, such as the mapping device cable 110. In some embodiments, the mapping device 130 is similar to the mapping device 100. In some embodiments, the marker 132 is similar to the marker 102. In some embodiments, the mapping electrode 134 is similar to at least one of the mapping electrodes 106. In some embodiments, the mapping electrode 134 is similar to each and every one of the mapping electrodes 106.

The mapping electrode 134 is shaped to provide stimulation to the tissue of the baroreceptor region. The mapping electrode 134 has a circular shape and the mapping device 130 includes a through-hole aperture 138 that extends through an interior region 140 of the mapping electrode 134. This results in the mapping electrode 134 having a circular closed curve shape or donut shape, where the interior region 140 of the mapping electrode 134 includes the through-hole aperture 138, which is surrounded by the conductive material of the mapping electrode 134. The marker 132 can be attached to the tissue of the baroreceptor region through the through-hole aperture 138. In some embodiments, the mapping electrode 134 has a different closed curve shape, such as a rectangular closed curve shape or a hexagonal closed curve shape. In some embodiments, the through-hole aperture 138 extends through the mapping device 130 next to the mapping electrode 134, and not through the interior region 140 of the mapping electrode 134.

Figure 5:
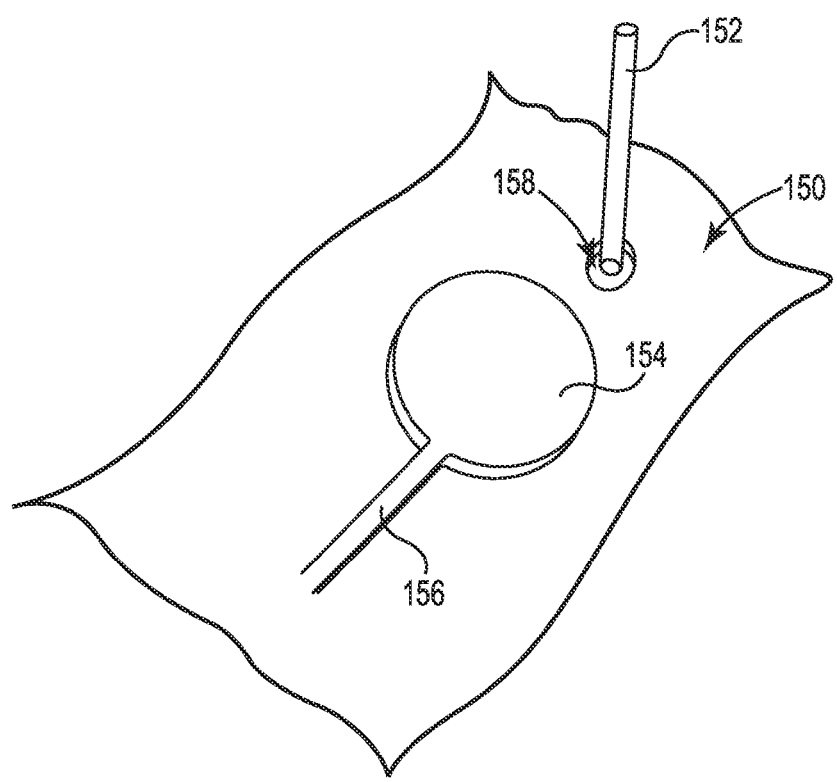
FIG. 5 is a diagram illustrating a mapping device and a marker, where the mapping device includes a through-hole aperture next to a mapping electrode, according to some embodiments described in the disclosure.

FIG. 5 is a diagram illustrating a mapping device 150 and a marker 152, where the mapping device 150 includes a through-hole aperture 158 that extends through the mapping device 150 next to a mapping electrode 154, according to some embodiments described in the disclosure. The mapping device 150 includes the mapping electrode 154 that is made from a conductive material and includes a conductive lead 156 that can be electrically coupled to a mapping device cable, such as the mapping device cable 110. In some embodiments, the mapping device 150 is similar to the mapping device 100. In some embodiments, the marker 152 is similar to the marker 102. In some embodiments, the mapping electrode 154 is similar to at least one of the mapping electrodes 106. In some embodiments, the mapping electrode 154 is similar to each and every one of the mapping electrodes 106.

The mapping electrode 154 is shaped to provide stimulation to the tissue of the baroreceptor region. The mapping electrode 154 has a circular shape and the mapping device 150 includes the through-hole aperture 158 that is situated next to the mapping electrode 154. The marker 152 can be attached to the tissue of the baroreceptor region through the through-hole aperture 158. In some embodiments, the mapping electrode 154 has a different shape, such as a rectangular shape or a hexagonal shape.

FIGS. 6A-6F are diagrams illustrating different markers 170, 172, 174, 176, 178, and 180 that can be attached to the tissue of the patient to indicate and keep track of the identified effective location in the baroreceptor region, according to some embodiments described in the disclosure.

Figure 6A:
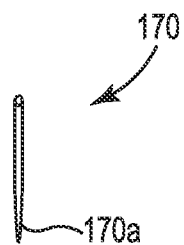
FIG. 6A is a diagram illustrating a marker that has a straight pin shape, according to some embodiments described in the disclosure.

FIG. 6A is a diagram illustrating a marker 170 that has a straight pin shape, according to some embodiments. The marker 170 includes an end 170a that is stuck into the tissue of the patient. In some embodiments, the marker 170 is a rigid pin. In some embodiments, the marker 170 is a rigid pin that includes metal.

Figure 6B:
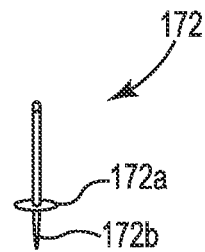
FIG. 6B is a diagram illustrating a marker that has a straight pin shape and includes an insertion stop, according to some embodiments described in the disclosure.

FIG. 6B is a diagram illustrating a marker 172 that has a straight pin shape and includes an insertion stop 172a, according to some embodiments. The marker 172 includes an end 172b that is inserted into the tissue of the patient and the insertion stop 172a prevents or stops further insertion of the marker 172 into the patient. In some embodiments, the marker 172 including the insertion stop 172a is rigid. In some embodiments, at least the insertion stop 172a is flexible. In some embodiments, the marker 172 includes metal.

Figure 6C:
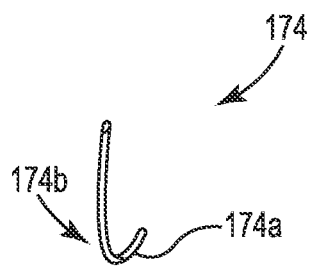
FIG. 6C is a diagram illustrating a marker that has a hook at one end of the marker, according to some embodiments described in the disclosure.

FIG. 6C is a diagram illustrating a marker 174 that has a hook 174a at one end 174b of the marker 174, according to some embodiments. The hook 174a is hooked through the tissue of the patient to attach the marker 174 to the patient. In some embodiments, the marker 174 is rigid. In some embodiments, the marker 174 includes metal.

Figure 6D:
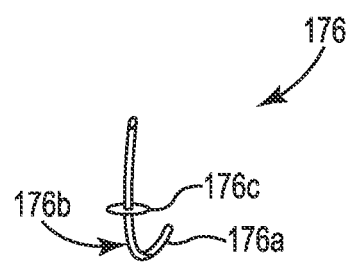
FIG. 6D is a diagram illustrating a marker that has a hook at one end of the marker and includes an insertion stop, according to some embodiments described in the disclosure.

FIG. 6D is a diagram illustrating a marker 176 that has a hook 176a at one end 176b and includes an insertion stop 176c, according to some embodiments. The hook 176a is hooked through the tissue of the patient to attach the marker 176 to the patient and the insertion stop 176c prevents or stops further insertion of the marker 176 into the patient. In some embodiments, the marker 176 including the insertion stop 176c is rigid. In some embodiments, at least the insertion stop 176c is flexible. In some embodiments, the marker 176 includes metal.

Figure 6E:
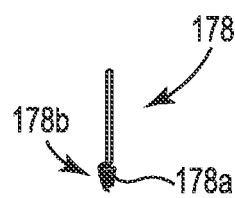
FIG. 6E is a diagram illustrating a marker that has a helix at one end of the marker, according to some embodiments described in the disclosure.

FIG. 6E is a diagram illustrating a marker 178 that has a helix 178a at one end 178b of the marker 178, according to some embodiments. The helix 178a is twisted into the tissue of the patient to attach the marker 178 to the patient. In some embodiments, the marker 178 is rigid. In some embodiments, the marker 178 includes metal.

Figure 6F:
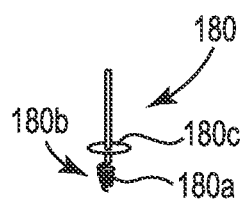
FIG. 6F is a diagram illustrating a marker that has a helix at one end of the marker and includes an insertion stop, according to some embodiments described in the disclosure.

FIG. 6F is a diagram illustrating a marker 180 that has a helix 180a at one end 180b and includes an insertion stop 180c, according to some embodiments. The helix 180a is twisted into the tissue of the patient to attach the marker 180 to the patient and the insertion stop 180c prevents or stops further insertion of the marker 180 into the patient. In some embodiments, the marker 180 including the insertion stop 180c is rigid. In some embodiments, at least the insertion stop 180c is flexible. In some embodiments, the marker 180 includes metal.

Figures 7A, 7B:
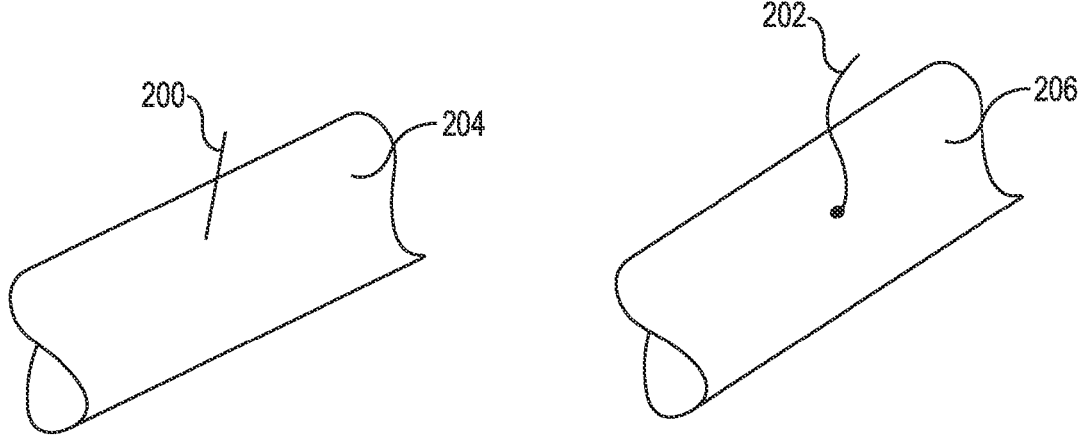
FIG. 7A is a diagram illustrating a pin shaped marker attached to an artery after the mapping device has been removed from the artery, according to some embodiments described in the disclosure.
FIG. 7B is a diagram illustrating a thread marker attached to an artery after the mapping device has been removed from the artery, according to some embodiments described in the disclosure.

FIGS. 7A and 7B are diagrams illustrating markers 200 and 202 attached to arteries 204 and 206, respectively, after a mapping device has been removed from the arteries 204 and 206, according to some embodiments described in the disclosure. In some embodiments, the markers 200 and 202 are similar to the marker 26 (shown in FIG. 1). In some embodiments, the markers 200 and 202 are similar to the marker 102 (shown in FIG. 2).

As previously described, a mapping device, such as the mapping device 22 and the mapping device 100, is used to map the baroreceptor region of the patient and the map is analyzed to determine which of the mapping electrodes, when stimulated, provides an effective physiological response. The location of this mapping electrode on the baroreceptor region is referred to as the identified effective location in the baroreceptor region. At least one marker, such as the marker 26 and the marker 102, is attached to the patient to indicate and keep track of the identified effective location in the baroreceptor region. The marker is attached to the patient in relation to the mapping device and the mapping electrode that, when stimulated, provided the effective physiological response. The marker indicates and keeps track of the identified effective location in the baroreceptor region. The marker maintains its location on the patient as the mapping device is removed and after the mapping device has been removed from the patient.

FIG. 7A is a diagram illustrating a marker 200 attached to the artery 204 after the mapping device has been removed from the artery 204, according to some embodiments. The marker 200 can be one of the markers 170, 172, 174, and 176.

In some embodiments, the marker 200 was attached to the tissue of the artery 204 through a through-hole aperture, such as the through-hole aperture 138 that extends through the mapping electrode 134 (shown in FIG. 4). The mapping electrode 134 may have been identified as the mapping electrode that, when stimulated, provides the most effective physiological response and the marker 200 is attached to the baroreceptor region at the identified effective location in the baroreceptor region of the patient.

In some embodiments, the marker 200 was attached to the tissue of the artery 204 through a through-hole aperture, such as the through-hole aperture 158 that is next to the mapping electrode 154 (shown in FIG. 5). The mapping electrode 154 may have been identified as the mapping electrode that, when stimulated, provides the most effective physiological response and the marker 200 is attached to the baroreceptor region just above the identified effective location in the baroreceptor region of the patient.

FIG. 7B is a diagram illustrating a marker 202 attached to the artery 206 after the mapping device has been removed from the artery 206, according to some embodiments. The marker 202 is a thread that has been sutured into the tissue of the artery 206.

In some embodiments, the marker 202 was attached to the tissue of the artery 206 through a through-hole aperture, such as the through-hole aperture 138 that extends through the mapping electrode 134 (shown in FIG. 4). The mapping electrode 134 may have been identified as the mapping electrode that, when stimulated, provides the most effective physiological response and the marker 202 is attached to the baroreceptor region at the identified effective location in the baroreceptor region of the patient.

In some embodiments, the marker 202 was attached to the tissue of the artery 206 through a through-hole aperture, such as the through-hole aperture 158 that is next to the mapping electrode 154 (shown in FIG. 5). The mapping electrode 154 may have been identified as the mapping electrode that, when stimulated, provides the most effective physiological response and the marker 202 is attached to the baroreceptor region just above the identified effective location in the baroreceptor region of the patient.

In some embodiments, one or more markers, such as the marker 200 and the marker 202, are attached to the tissue of the arteries 204 and 206 through one or more through-hole apertures in the mapping device. In some embodiments, one or more markers, such as the marker 200 and the marker 202, are attached to the tissue of the arteries 204 and 206 through one or more through-hole apertures in the periphery of the mapping device. In some embodiments, one or more markers, such as the marker 200 and the marker 202, are attached to the tissue of the arteries 204 and 206 next to the mapping device.

Figure 8:
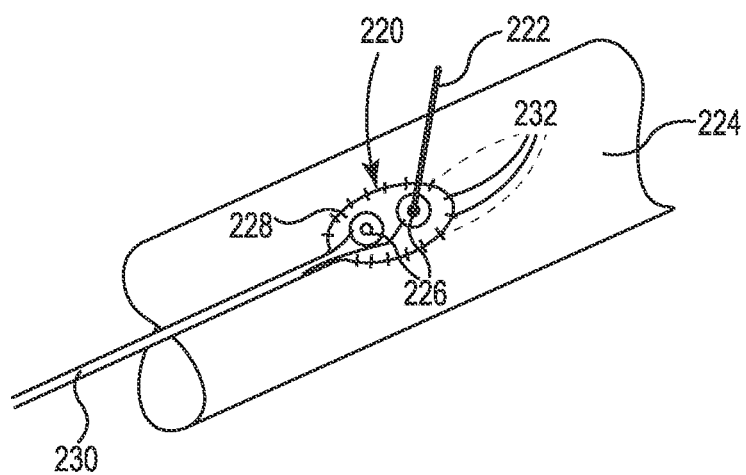
FIG. 8 is a diagram illustrating an implantable device and a marker attached to an artery, according to some embodiments described in the disclosure.

FIG. 8 is a diagram illustrating an implantable device 220 and a marker 222 attached to an artery 224, according to some embodiments described in the disclosure. The implantable device 220 can be sutured onto the artery 224 to provide long term stimulation of the baroreceptors at the identified effective location in the baroreceptor region. In some embodiments, an implantable medical device is electrically coupled to the implantable device 220 to provide electrical stimulation to the patient.

The marker 222 is attached to the artery 224 to indicate and keep track of the identified effective location in the baroreceptor region. In some embodiments, multiple markers, such as marker 222, can be attached to the artery 224 to indicate and keep track of the identified effective location in the baroreceptor region. In some embodiments, the marker 222 is similar to one or more of the markers described in this disclosure, including the markers 26, 102, 132, 152, 170, 172, 174, 176, 200, and 202.

The implantable device 220 has a first side facing the artery 224 and a second side that opposes the first side and faces away from the artery 224. The implantable device 220 includes one or more implantable electrodes 226 formed on a substrate 228. The substrate 228 includes at least one insulating layer on the first side of the implantable device 220 and the implantable electrodes 226 are formed on the insulating layer of the substrate 228. The implantable electrodes 226 are situated on the first side to face the artery 224 and contact the tissue of the baroreceptor region. In some embodiments, each of the implantable electrodes 226 is electrically isolated from the other implantable electrodes 226 on the substrate 228. In some embodiments, the implantable device 220 is built using printed circuit board technology.

The implantable electrodes 226 are made out of a conductive material and electrically coupled to an implantable device cable 230, which can be electrically coupled to a stimulator, such as a stimulator in an implantable medical device. In some embodiments, the implantable electrodes 226 include metal. In some embodiments, the implantable electrodes 226 include copper.

The implantable device 220 is aligned on the artery 224 using the marker 222 and one of the implantable electrodes 226 is situated on the identified effective location. The implantable device 220 is sutured into place on the artery 224 with sutures 232 and the implantable electrode 226 is used to provide stimulation of the baroreceptors at the identified effective location in the baroreceptor region. After the implantable device 220 is attached to the patient, the marker 222 is removed from the patient. In some embodiments, multiple markers can be used to keep track of the identified effective location on the baroreceptor region and removed after the implantable device 220 is attached to the patient.

In some embodiments, the implantable device 220 includes an aligning aperture that is slid over the marker 222 attached to the patient. The marker 222 is slid through the aligning aperture to align the implantable device 220 and one of the implantable electrodes 226 on the identified effective location in the baroreceptor region. The marking aperture can be a through-hole aperture in the implantable device 220, which extends completely through the implantable device 220, from the first side of the implantable device 220 to the second side of the implantable device 220. In some embodiments, the implantable device 220 includes a through-hole aperture through each of the implantable electrodes 226 and the marker 224 is slid through one of these through-hole apertures to align the implantable device 220 on the artery 224. In some embodiments, the implantable device 220 includes a through-hole aperture next to each of the implantable electrodes 226 and the marker 222 is slid through one of these through-hole apertures to align the implantable device 220 on the artery 224. In some embodiments, the implantable device 220 includes one or more through-hole apertures at the periphery of the implantable device 220, outside the implantable electrodes 226, and one or more markers, such as marker 222, is slid through one or more of these through-hole apertures to align the implantable device 220 on the artery 224.

Figure 9:
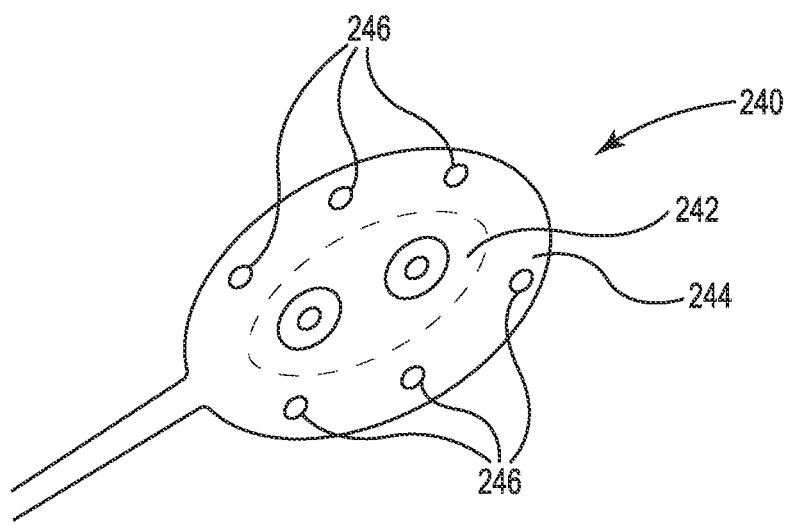
FIG. 9 is a diagram illustrating an implantable device including an implantable electrode region and a periphery region, according to some embodiments described in the disclosure.

FIG. 9 is a diagram illustrating an implantable device 240 including an implantable electrode region 242 and a periphery region 244 that is outside the implantable electrode region 242 as indicated by dashed lines, according to some embodiments described in the disclosure. In some embodiments, the implantable device 240 is similar to the implantable device 220.

The implantable electrode region 242 includes the implantable electrodes, such as the implantable electrodes 226, and the periphery region 244 includes through-hole apertures 246 that extend through the implantable device 240. Markers, such as marker 222, can be slid through one or more of the through-hole apertures 246 to align the implantable device 240 on the patient.

Figure 10:
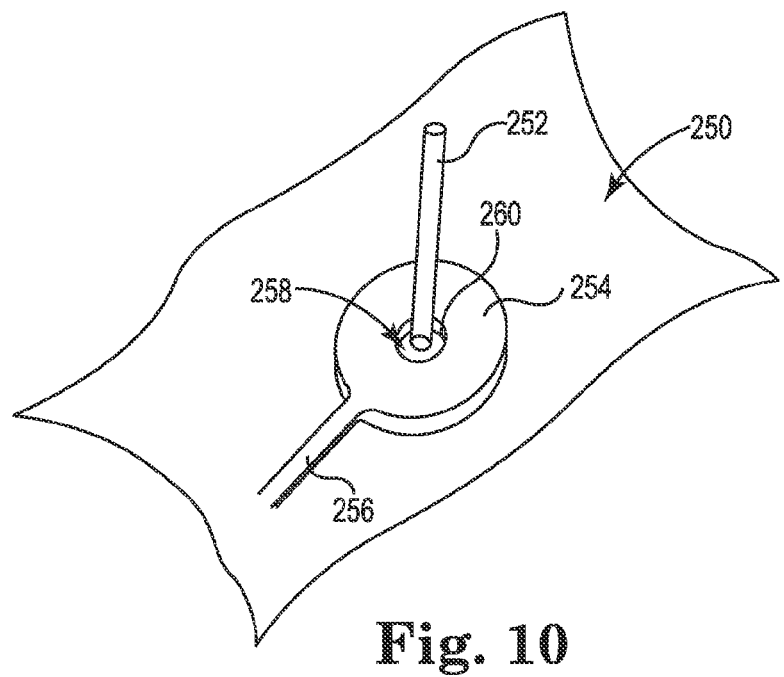
FIG. 10 is a diagram illustrating an implantable device and a marker, where the implantable device includes a through-hole aperture through an implantable electrode, according to some embodiments described in the disclosure.

FIG. 10 is a diagram illustrating an implantable device 250 and a marker 252, according to some embodiments described in the disclosure. The implantable device 250 includes an implantable electrode 254 that is made from a conductive material and includes a conductive lead 256 that can be electrically coupled to an implantable device cable, such as the implantable device cable 230. In some embodiments, the implantable device 250 is similar to the implantable device 220. In some embodiments, the marker 252 is similar to the marker 222. In some embodiments, the implantable electrode 254 is similar to at least one of the implantable electrodes 226. In some embodiments, the implantable electrode 254 is similar to each and every one of the implantable electrodes 226.

The implantable electrode 254 is shaped to provide stimulation to the tissue of the baroreceptor region. The implantable electrode 254 has a circular shape and the implantable device 250 includes a through-hole aperture 258 that extends through an interior region 260 of the implantable electrode 254. This results in the implantable electrode 254 having a circular closed curve shape or donut shape, where the interior region 260 of the implantable electrode 254 includes the through-hole aperture 258, which is surrounded by the conductive material of the implantable electrode 254. The marker 252 is slid through the through-hole aperture 258 to align the implantable device 250 and the implantable electrode 256 on the identified effective location in the baroreceptor region. In some embodiments, the implantable electrode 254 has a different closed curve shape, such as a rectangular closed curve shape or a hexagonal closed curve shape. In some embodiments, the through-hole aperture 258 extends through the implantable device 250 next to the implantable electrode 254, and not through the interior region 260 of the implantable electrode 254.

Figure 11:
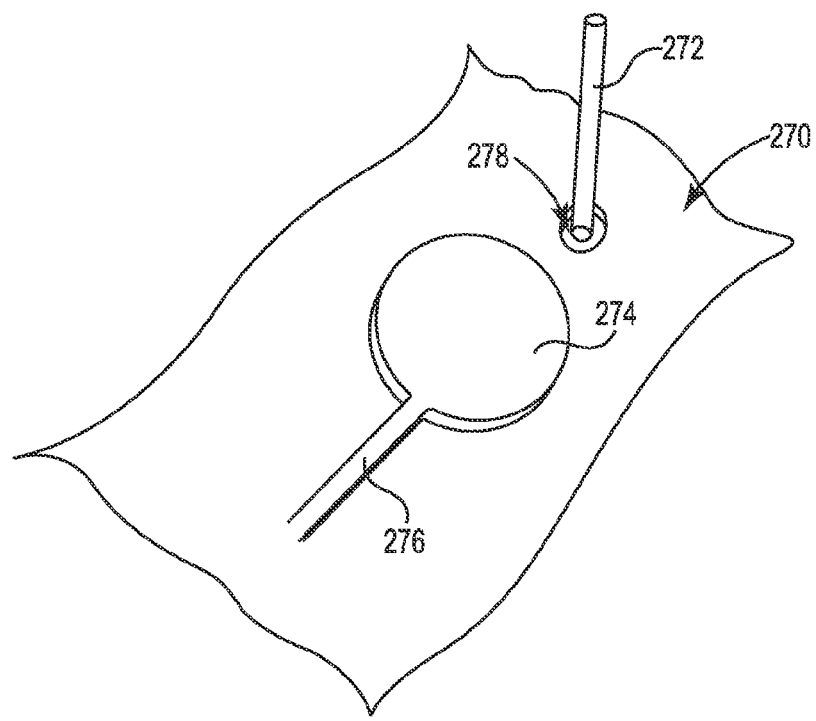
FIG. 11 is a diagram illustrating an implantable device and a marker, where the implantable device includes a through-hole aperture next to an implantable electrode, according to some embodiments described in the disclosure.

FIG. 11 is a diagram illustrating an implantable device 270 and a marker 272, where the implantable device 270 includes a through-hole aperture 278 that extends through the implantable device 270 next to an implantable electrode 274, according to some embodiments described in the disclosure. The implantable device 270 includes the implantable electrode 274 that is made from a conductive material and includes a conductive lead 276 that can be electrically coupled to an implantable device cable, such as the implantable device cable 230. In some embodiments, the implantable device 270 is similar to the implantable device 220. In some embodiments, the marker 272 is similar to the marker 222. In some embodiments, the implantable electrode 274 is similar to at least one of the implantable electrodes 226. In some embodiments, the implantable electrode 274 is similar to each and every one of the implantable electrodes 226.

The implantable electrode 274 is shaped to provide stimulation to the tissue of the baroreceptor region. The implantable electrode 274 has a circular shape and the implantable device 270 includes the through-hole aperture 278 that is situated next to the implantable electrode 274. The marker 272 is slid through the through-hole aperture 278 to align the implantable device 270 and the implantable electrode 276 on the identified effective location in the baroreceptor region. In some embodiments, the implantable electrode 274 has a different shape, such as a rectangular shape or a hexagonal shape.

Figure 12:
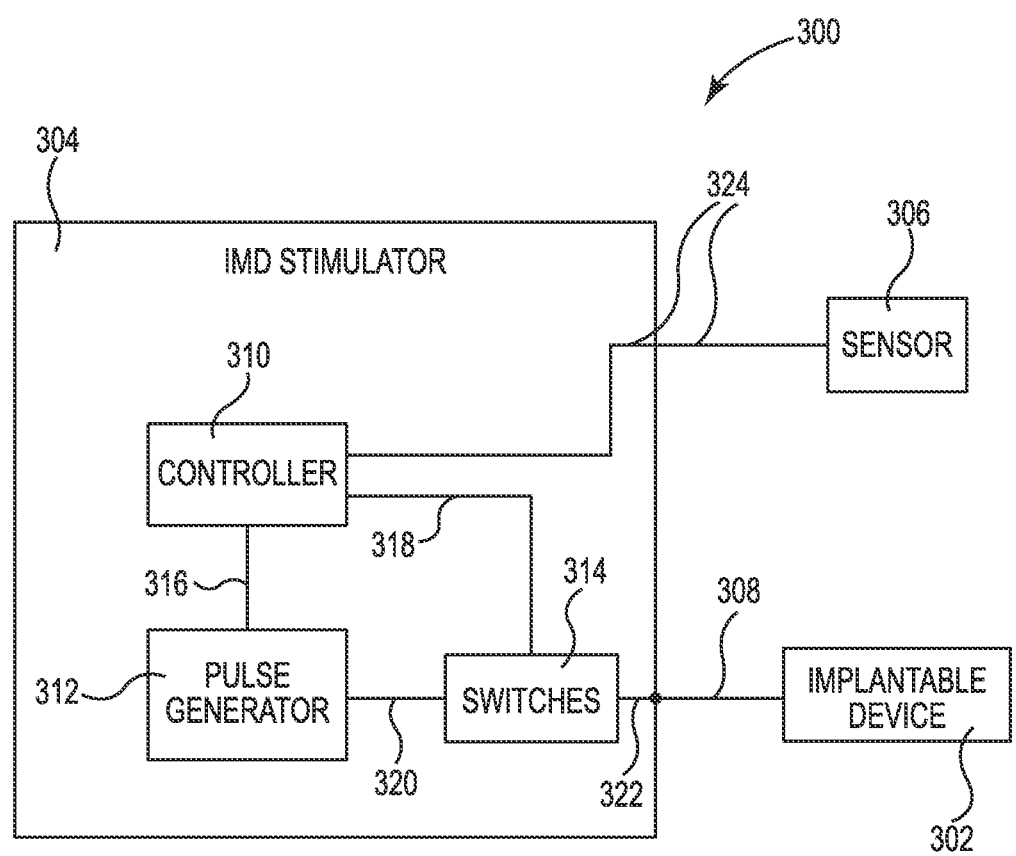
FIG. 12 is a diagram illustrating an example of an implantable system, according to some embodiments described in the disclosure.

FIG. 12 is a diagram illustrating an example of an implantable system 300 coupled to an implantable device 302 for long term stimulation of the baroreceptors at the identified effective location in the baroreceptor region of a patient, according to some embodiments described in the disclosure. The implantable system 300 can be electrically coupled to any of the implantable devices described in this disclosure, including the implantable devices 220, 240, 250, and 270, for providing electrical stimulation to the baroreceptors in a baroreceptor region. The implantable system 300 can be used to provide electrical stimulation to the baroreceptors in baroreceptor regions such as the carotid sinus of the ICA, the carotid sinus of the ECA, the area near the bifurcation of the ICA and the ECA, the arch of the aorta artery, and others.

The implantable system 300 includes the implantable device 302, an implantable medical device (IMD) stimulator 304, and a sensor 306. The implantable device 302 is similar to one or more of the implantable devices 220, 240, 250, and 270, and electrically coupled to the IMD stimulator 304 by an implantable device cable 308.

The IMD stimulator 304 includes an IMD controller 310, an IMD pulse generator 312, and IMD switches 314. The controller 310 is communicatively coupled to the pulse generator 312 via communications path 316 and to the switches 314 via communications path 318. The pulse generator 312 is electrically coupled to the switches 314 via conductive path 320, and the switches 314 are electrically coupled to the implantable device 302 via conductive path 322 and the cable 308. Also, the controller 310 is communicatively coupled to the sensor 306 via communications path 324.

The controller 310 receives signals from the sensor 306, which indicate the physiological state of the patient. The controller 310 analyzes the signals to determine whether the patient needs electrical stimulation through the implantable device 302 and, if so, the parameters of the electrical stimulation, including one or more of amplitude, pulse width, pulse frequency, burst duration for a train of pulses, burst cycle duration, and duty cycle. In some embodiments, the controller 310 stores the physiological data obtained from the patient via the sensor 306.

The controller 310 controls the switches 314 to selectively connect one or more implantable electrodes in the implantable device 302 to the pulse generator 312, and the controller 310 controls the pulse generator 312 to stimulate the connected implantable electrodes. In some embodiments, the controller 310 controls the switches 314 to connect one or more of the implantable electrodes to the pulse generator 312 as cathodes and/or one or more of the implantable electrodes as anodes. In some embodiments, the pulse generator 312 controls the switches 314 to connect two or more of the implantable electrodes to the pulse generator 312 for bipolar stimulation, i.e., at least one cathode electrode and at least one anode electrode. In some embodiments, the controller 310 controls the switches 314 to connect one implantable electrode to the pulse generator 312 for unipolar stimulation.

Figure 13:
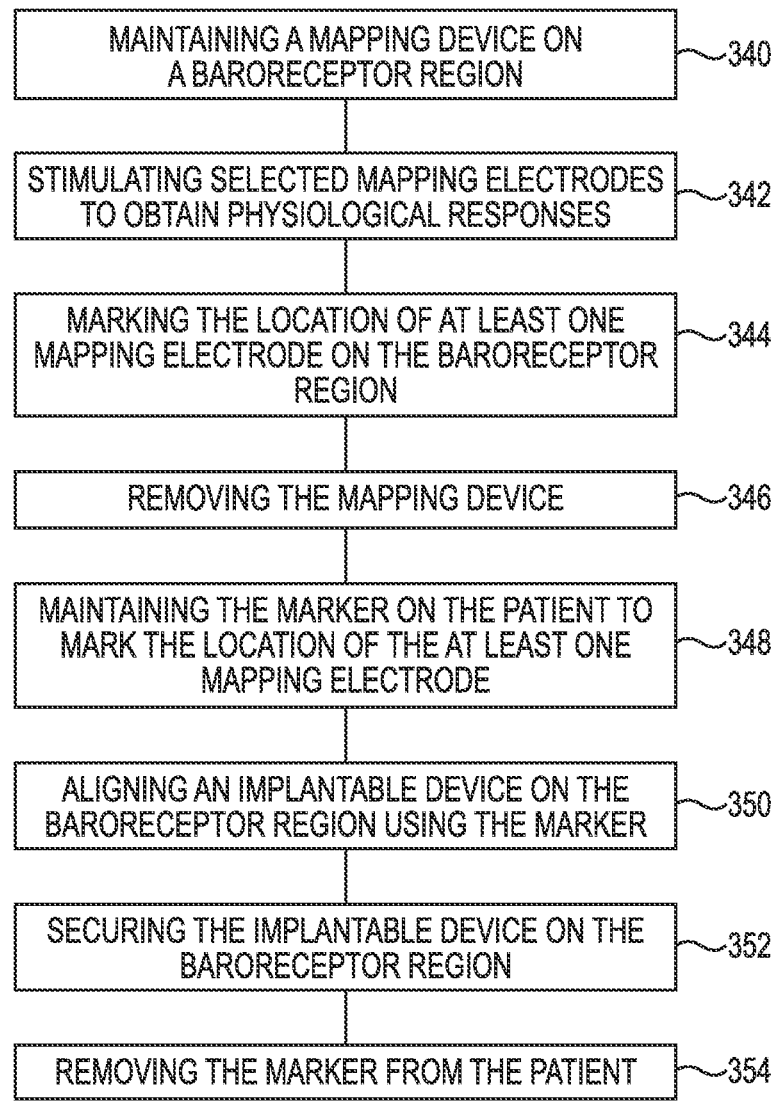
FIG. 13 is a flow chart diagram illustrating a method of mapping a baroreceptor region, marking an identified effective location in the baroreceptor region, and attaching an implantable device on the baroreceptor region at the identified effective location, according to some embodiments described in the disclosure.

FIG. 13 is a flow chart diagram illustrating the method of mapping a baroreceptor region, marking an identified effective location in the baroreceptor region, and attaching an implantable device on the baroreceptor region at the identified effective location, according to some embodiments described in the disclosure.

The method, at 340, includes the step of maintaining a mapping device on the baroreceptor region. The mapping device includes a plurality of mapping electrodes that are situated on the baroreceptor region. In some embodiments, the mapping device is similar to one or more of the mapping devices 22, 100, 120, 130, 150, and 404. In some embodiments, the mapping device is a self-curling mapping device that wraps around at least one part of the patient, such as an artery, to maintain the mapping device and the mapping electrodes on the baroreceptor region. In some embodiments, the backing of the mapping device is formed to curl the mapping device around at least one part of the patient, such as an artery, to maintain the mapping device and the mapping electrodes on the baroreceptor region. In some embodiments, the substrate is formed to curl the mapping device around at least one part of the patient, such as an artery, to maintain the mapping device and the mapping electrodes on the baroreceptor region. In some embodiments, the mapping device includes a self-curling sheet that curls the mapping device around at least one part of the patient, such as an artery, to maintain the mapping device and the mapping electrodes on the baroreceptor region.

At 342, the method includes the step of stimulating selected mapping electrodes of the plurality of mapping electrodes on the baroreceptor region with a stimulator, such as stimulator 24, to obtain physiological responses from the patient. The physiological responses are in response to electrical stimulation of the baroreceptors in the baroreceptor region under the stimulated mapping electrodes.

In some embodiments, a sensor, such as sensor 36, senses at least one physiological parameter of the patient and provides signals that indicate the sensed physiological parameter. The stimulator receives these signals and analyzes the signals to obtain the physiological response of the patient due to the electrical stimulation of the baroreceptors in the baroreceptor region under the stimulated mapping electrodes. The stimulator stores the stimulated mapping electrode and physiological response information in a map of the baroreceptor region. In some embodiments, the stimulator analyzes the map of the baroreceptor region to identify the location of at least one of the selected electrodes that, when stimulated, provides an effective physiological response.

At 344, the method includes the step of marking the location of at least one of the selected mapping electrodes on the baroreceptor region of the patient with a marker based on the analysis of the physiological responses from the patient. The marker is attached to the patient relative to the mapping device and the location of the at least one mapping electrode that, when stimulated, provides an effective physiological response. In some embodiments, the marker is attached to the patient through at least one marking aperture that extends through the mapping device. In some embodiments, marking the location includes sticking a pin into the patient through at least one marking aperture that extends through the mapping device. In some embodiments, marking the location includes suturing a thread into the patient through at least one marking aperture that extends through the mapping device.

Next, at 346, the method includes the step of removing the mapping device from the patient and, at 348, maintaining the marker on the patient to mark the location of the at least one mapping electrode on the baroreceptor region of the patient. In some embodiments, the marker is maintained on the patient via a hook at one end of the marker.

At 350, the method includes the step of aligning an implantable device on the baroreceptor region using the attached marker. In some embodiments, aligning the implantable device on the baroreceptor region includes positioning the marker through at least one aligning aperture that extends through the implantable device. In some embodiments, the marker is a pin and aligning the implantable device on the baroreceptor region includes positioning the pin through at least one aligning aperture that extends through the implantable device. In some embodiments, the marker is a sutured thread and aligning the implantable device on the baroreceptor region includes positioning the thread through at least one aligning aperture that extends through the implantable device.

At 352, the method includes the step of securing, to the patient, the implantable device aligned with the marker on the baroreceptor region. Where, in some embodiments, securing the implantable device to the patient includes suturing the implantable device to the patient. At 354, the method includes the step of removing the marker from the patient.

FIGS. 14-18 are diagrams illustrating a method of attaching a mapping device 400 to a self-curling silicone sheet 402 to produce a self-curling mapping device 404, according to some embodiments described in the disclosure. The self-curling mapping device 404 can be wrapped or curled around a body part, such as an artery, to hold mapping electrodes 406 on a baroreceptor region. In some embodiments, the self-curling mapping device 404 is similar to one or more of the mapping devices described in this disclosure, including the mapping devices 22, 100, 120, 130, and 150.

Figure 14:
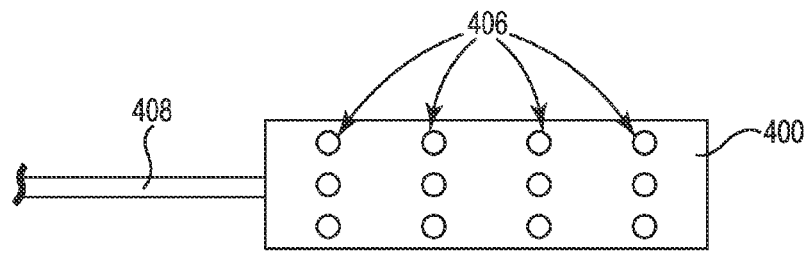
FIG. 14 is a diagram illustrating a mapping device prior to attaching a self-curling silicone sheet, according to some embodiments described in the disclosure.

FIG. 14 is a diagram illustrating the mapping device 400 prior to attaching the self-curling silicone sheet 402, according to some embodiments. The mapping device 400 includes the mapping electrodes 406 electrically coupled to a mapping device cable 408.

Figure 15:
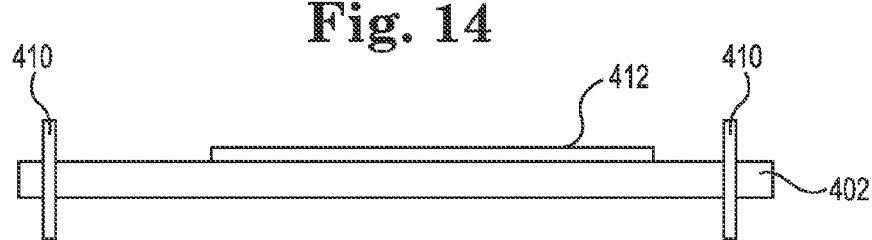
FIG. 15 is a diagram illustrating the self-curling silicone sheet, according to some embodiments described in the disclosure.

FIG. 15 is a diagram illustrating the self-curling silicone sheet 402, according to some embodiments. The self-curling silicone sheet 402 is unrolled and tacked or staked down by tacks 410 to a flat surface. A layer of silicone adhesive 412 is applied to at least part of the inward curling portion of the self-curling silicone sheet 402 for attaching the mapping device 400.

Figure 16:
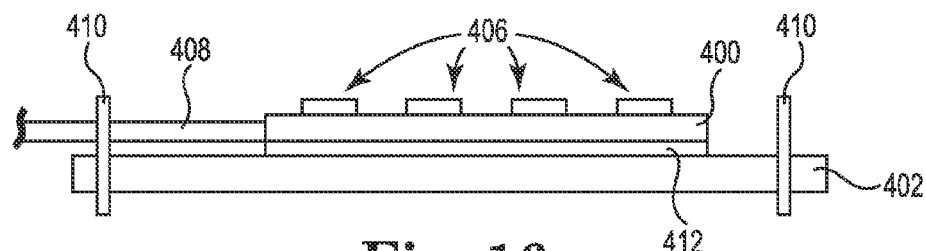
FIG. 16 is a diagram illustrating the mapping device attached to the self-curling silicone sheet by silicone adhesive, according to some embodiments described in the disclosure.

FIG. 16 is a diagram illustrating the mapping device 400 attached to the self-curling silicone sheet 402 by the silicone adhesive 412, according to some embodiments. The mapping device 400 is laminated onto the flattened self-curling silicone sheet 402 via the silicone adhesive 412. In some embodiments, the laminated assembly is then curled around a mandrel to allow the uncured silicone adhesive 412 to cure in the curled state, thereby seating the mapping device 400 properly and setting the curl as permanent. After curing, the self-curling mapping device 404 is uncurled and the periphery of the self-curling silicone sheet 402 is trimmed away to best fit or grip onto the body part of the patient.

Figure 17:
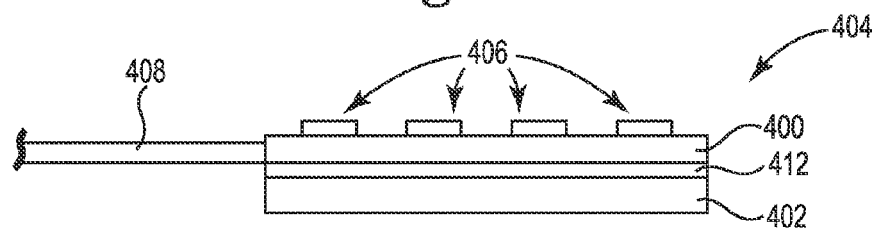
FIG. 17 is a diagram illustrating a flattened self-curling mapping device with the excess of the self-curling silicone sheet trimmed away, according to some embodiments described in the disclosure.

FIG. 17 is a diagram illustrating a flattened self-curling mapping device 404 with the excess of the self-curling silicone sheet 402 trimmed away, according to some embodiments.

Figure 18:
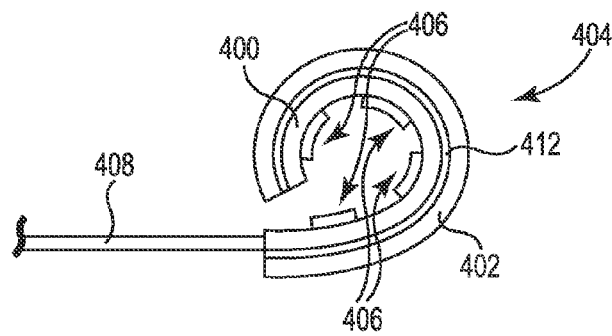
FIG. 18 is a diagram illustrating a curled self-curling mapping device, according to some embodiments described in the disclosure.

FIG. 18 is a diagram illustrating a curled self-curling mapping device 404, according to some embodiments. The self-curling mapping device 404 is uncurled during surgery and re-curled around a body part, such as an artery, to establish a mechanical fix or grip onto the artery.

Figure 19:
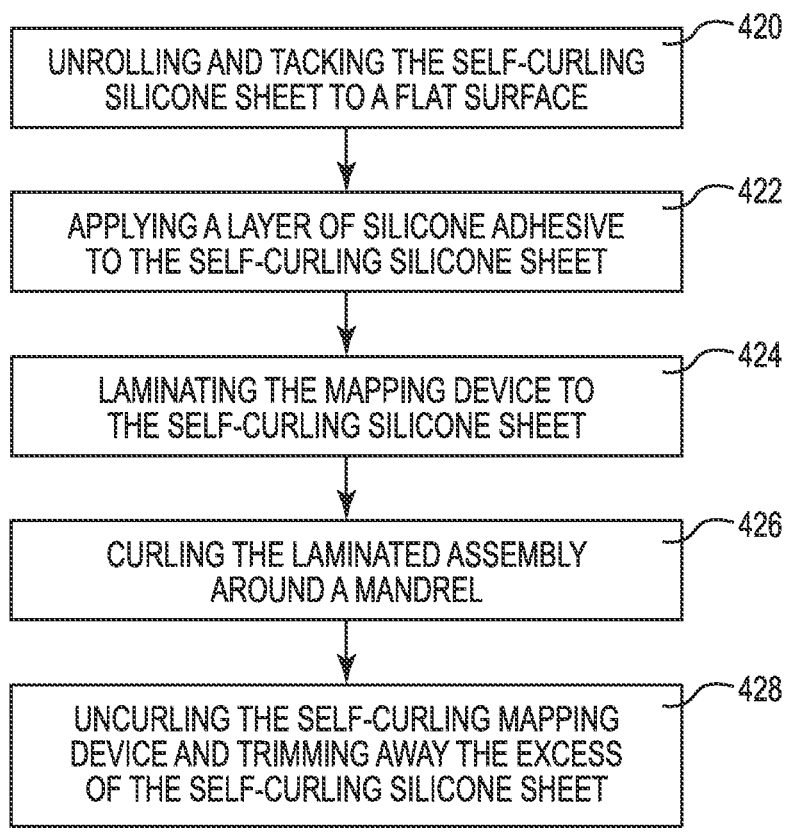
FIG. 19 is a flow chart diagram illustrating the method of producing the self-curling mapping device, according to some embodiments described in the disclosure.

FIG. 19 is a flow chart diagram illustrating the method of producing the self-curling mapping device 404, according to some embodiments described in the disclosure.

At 420, the method includes the step of unrolling and tacking the self-curling silicone sheet 402 to a flat surface. The self-curling silicone sheet 402 can be tacked down with tacks 410 to the flat surface. At 422, a layer of silicone adhesive 412 is applied to at least part of the inward curling portion of the self-curling silicone sheet 402 for attaching the mapping device 400.

At 424, the method includes the step of laminating or bonding the mapping device 400 onto the flattened self-curling silicone sheet 402 via the silicone adhesive 412. At 426, the method includes the step of curling the laminated assembly around a mandrel to allow the uncured silicone adhesive 412 to cure in the curled state, thereby seating the mapping device 400 properly and setting the curl as permanent.

At 428, the method includes the step of uncurling the self-curling mapping device 404 and trimming away the excess of the self-curling silicone sheet 402. The self-curling mapping device 404 is uncurled during surgery and re-curled around a part of the patient's body, such as an artery, to establish a mechanical fix or grip on the artery.

Alternatively, in some embodiments, the backing of a mapping device is formed to provide a self-curling mapping device that can curl or wrap around at least one part of the patient, such as an artery, to maintain the mapping device and the mapping electrodes on the baroreceptor region. In some embodiments, the substrate of the mapping device, such as substrate 108, is formed to provide a self-curling mapping device that can curl or wrap the mapping device around at least one part of the patient, such as an artery, to maintain the mapping device and the mapping electrodes on the baroreceptor region.

Some advantages of a self-curling mapping device, such as the self-curling mapping device 404, include: a method of fixing the self-curling mapping device onto the patient without the need of hand holding the mapping device in place during the mapping procedure; a method of fixing the self-curling mapping device in place without the use of a suture during the mapping procedure; a self-curling mapping device that is stable in its position on the patient thereby reducing or eliminating electrical noise caused by the movement of the self-curling mapping device during the mapping procedure; and a gripping method that allows convenient re-positioning on the patient.

FIGS. 20-25 are diagrams illustrating an algorithm for mapping the baroreceptors in a baroreceptor region of a patient. The mapping can be achieved utilizing a stimulator, such as the stimulator 24 (shown in FIG. 1).

Figure 20:
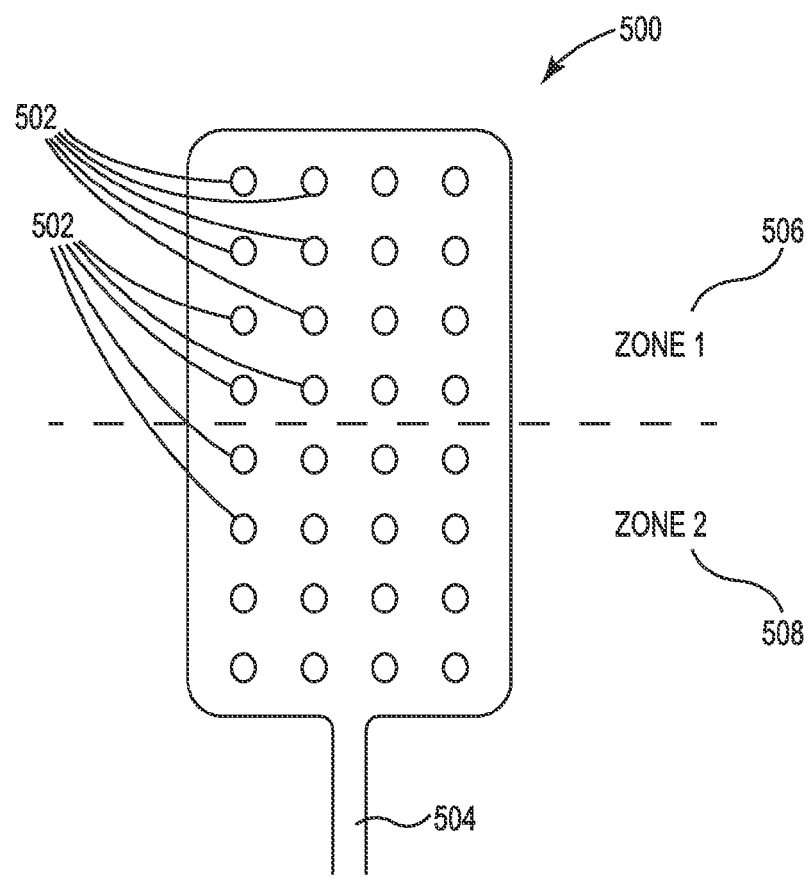
FIG. 20 is a diagram illustrating a mapping device that is used to map the targeted baroreceptor region, according to some embodiments.

FIG. 20 is a diagram illustrating a mapping device 500 that is used to map the targeted baroreceptor region, according to some embodiments. The mapping device 500 includes a plurality of mapping electrodes 502 that are electrically coupled to the stimulator 24 via mapping device cable 504. In some embodiments, the mapping device 500 is similar to one or more of the mapping devices described in this disclosure, including the mapping devices 22, 100, 120, 130, 150, and 404.

As used in this example, the stimulator 24 includes the stimulation controller 40, the stimulation pulse generator 42, and the switches 44. The controller 40 controls the switches 44 to selectively connect one or more of the mapping electrodes 502 to the pulse generator 42 as one or more cathodes and/or to selectively connect one or more of the mapping electrodes 502 to the pulse generator 42 as one or more anodes. Also, the controller 40 controls the pulse generator 42 to stimulate the baroreceptor region through the connected mapping electrodes 502, where the stimulation parameters can include one or more of amplitude, pulse width, pulse frequency, burst duration for a train of pulses, burst cycle duration, and duty cycle. The controller 40 controls the pulse generator 42 to provide unipolar electrical stimulation to the tissue of the baroreceptor region through the mapping electrodes 502 or bipolar electrical stimulation to the tissue of the baroreceptor region through the mapping electrodes 502.

In some embodiments, to provide unipolar stimulation, the controller 40 controls the switches 44 to selectively connect one of the mapping electrodes 502 to the pulse generator 42 as a cathode and the controller 40 controls the pulse generator 42 to stimulate the baroreceptor region through the connected mapping electrode. A circuit path is completed through the body of the patient to any suitable location on the patient.

In some embodiments, to provide bipolar stimulation, the controller 40 controls the switches 44 to selectively connect one of the mapping electrodes 502 to the pulse generator 42 as a cathode and to connect another of the mapping electrodes 502 to the pulse generator 42 as an anode. The controller 40 controls the pulse generator 42 to provide bipolar stimulation to the baroreceptor region through the connected mapping electrodes 502, where the circuit path is completed from anode to cathode or from cathode to anode.

In this example, the controller 40 receives the signals from the sensor 36 and analyzes the signals to obtain the physiological responses from the patient. The controller 40 stores the data in a map of the baroreceptor region, indicating the mapping electrode of the mapping electrodes 502 that was stimulated and the corresponding physiological response. In addition, the controller 40 analyzes the map of the baroreceptor region to determine which zones of the mapping electrodes 502 are most likely to include the mapping electrode of the mapping electrodes 502 that, when stimulated, provides the effective physiological response. The location of this mapping electrode is referred to herein as the identified effective location in the baroreceptor region.

To begin, the stimulator 24 divides the mapping device 500 into two zones of mapping electrodes 502, a zone 1 at 506 and a zone 2 at 508 as indicated by the dashed line. The zone 1 at 506 includes the mapping electrodes 502 in the upper half of the mapping device 500 and the zone 2 at 508 includes the mapping electrodes 502 in the lower half of the mapping device 500. Next, for mapping the baroreceptor region under the mapping electrodes 502 in zone 1 at 506, the controller 40 controls the switches 44 to connect one of the mapping electrodes 502 in zone 1 at 506 to the pulse generator 42 as a cathode and one or more of the mapping electrodes in zone 2 at 508 as an anode. The controller 40 controls the pulse generator 42 to provide bipolar stimulation to the baroreceptor region through the connected mapping electrodes 502. Alternatively, in some embodiments, the controller 40 and the pulse generator 42 provide unipolar stimulation to the one of the mapping electrodes 502 connected as a cathode.

The controller 40 receives the signals from the sensor 36 and analyzes the signals to obtain the physiological response from the patient, which is in response to stimulation of the baroreceptor region under the cathode connected mapping electrode. The controller 40 stores the data in the map of the baroreceptor region, indicating the cathode connected mapping electrode that was stimulated and the corresponding physiological response. This process can be repeated for each of the mapping electrodes in zone 1 at 506 to complete the map of the baroreceptor region under the mapping electrodes 502 in zone 1 at 506. In some embodiments, this process can be repeated for a select number of mapping electrodes, such as two or three mapping electrodes, in zone 1 at 506 to complete the map of the baroreceptor region under the mapping electrodes 502 in zone 1 at 506.

Next, for mapping the baroreceptor region under the mapping electrodes 502 in zone 2 at 508, the controller 40 controls the switches 44 to connect one of the mapping electrodes 502 in zone 2 at 508 to the pulse generator 42 as a cathode and one or more of the mapping electrodes in zone 1 at 506 as an anode. The controller 40 controls the pulse generator 42 to provide bipolar stimulation to the baroreceptor region through the connected mapping electrodes 502. Alternatively, in some embodiments, the controller 40 and the pulse generator 42 provide unipolar stimulation to the one of the mapping electrodes 502 connected as a cathode.

The controller 40 receives the signals from the sensor 36 and analyzes the signals to obtain the physiological response from the patient, which is in response to stimulation of the baroreceptor region under the cathode connected mapping electrode. The controller 40 stores the data in the map of the baroreceptor region, indicating the cathode connected mapping electrode that was stimulated and the corresponding physiological response. This process can be repeated for each of the mapping electrodes in zone 2 at 508 to complete the map of the baroreceptor region under the mapping electrodes 502 in zone 2 at 508. In some embodiments, this process can be repeated for a select number of mapping electrodes, such as two or three mapping electrodes, in zone 2 at 508 to complete the map of the baroreceptor region under the mapping electrodes 502 in zone 2 at 508.

Next, the controller 40 analyzes the maps of the baroreceptor region to determine which zone of zone 1 at 506 and zone 2 at 508 is most likely to include the mapping electrode or mapping electrodes that, when stimulated, provide the effective physiological response. The zone that is most likely to include this mapping electrode is selected and the process continues. In some embodiments, the effective physiological response is the largest reduction in the blood pressure of the patient. In some embodiments, the effective physiological response is the largest reduction in the heart rate of the patient. In some embodiments, the effective physiological response is the largest change in the tissue impedance of the patient.

In some embodiments, the controller 40 displays the map of the baroreceptor region and, after viewing the map of the baroreceptor region, a user selects one of the two zones. In some embodiments, the controller 40 selects the zone that is most likely to include the mapping electrode or mapping electrodes that, when stimulated, provide the effective physiological response. In some embodiments, the controller 40 selects the zone by comparing the individual physiological response values in one zone to the individual physiological response values in the other zone and selecting the zone that has the largest physiological response value. In some embodiments, the controller 40 selects the zone by averaging the physiological response values in one zone and averaging the physiological response values in the other zone and selecting the zone that provides the largest average physiological response value. In some embodiments, the controller 40 selects the zone by summing the physiological response values in one zone and summing the physiological response values in the other zone and selecting the zone that provides the largest sum.

Figure 21:
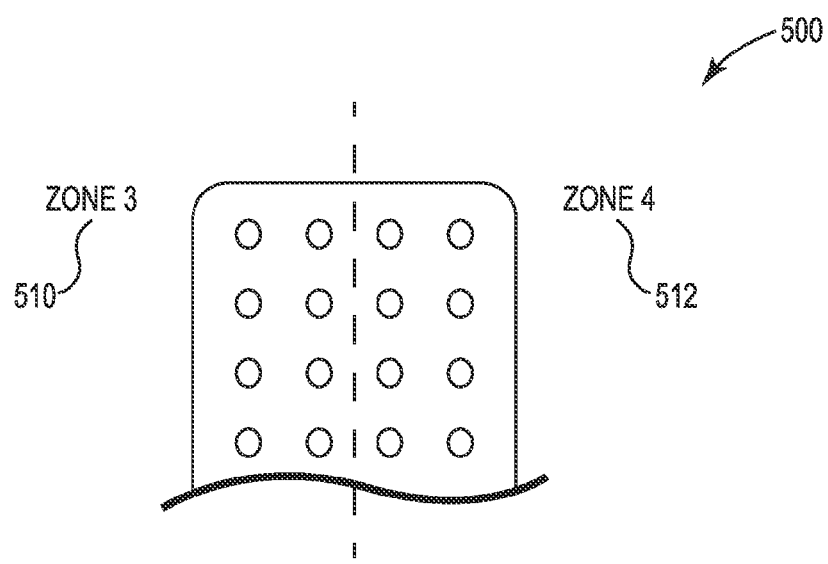
FIG. 21 is a diagram illustrating the selection of zone 1 and the division of zone 1 into a zone 3 and a zone 4, according to some embodiments described in the disclosure.

FIG. 21 is a diagram illustrating the selection of zone 1 at 506 and the division of zone 1 at 506 into a zone 3 at 510 and a zone 4 at 512 as indicated by the dashed line and according to some embodiments described in the disclosure. The zone 3 at 510 includes the mapping electrodes 502 in the left side of zone 1 at 506 and the zone 4 at 512 includes the mapping electrodes 502 in the right side of zone 1 at 506. Next, for mapping the baroreceptor region under the mapping electrodes 502 in zone 3 at 510, the controller 40 controls the switches 44 to connect one of the mapping electrodes 502 in zone 3 at 510 to the pulse generator 42 as a cathode and one or more of the mapping electrodes in zone 4 at 512 as an anode. The controller 40 controls the pulse generator 42 to provide bipolar stimulation to the baroreceptor region through the connected mapping electrodes 502. Alternatively, in some embodiments, the controller 40 and the pulse generator 42 provide unipolar stimulation to the one of the mapping electrodes 502 connected as a cathode.

The controller 40 receives the signals from the sensor 36 and analyzes the signals to obtain the physiological response from the patient, which is in response to stimulation of the baroreceptor region under the cathode connected mapping electrode. The controller 40 stores the data in the map of the baroreceptor region, indicating the cathode connected mapping electrode that was stimulated and the corresponding physiological response. This process can be repeated for each of the mapping electrodes in zone 3 at 510 to complete the map of the baroreceptor region under the mapping electrodes 502 in zone 3 at 510. In some embodiments, this process can be repeated for a select number of mapping electrodes, such as two or three mapping electrodes, in zone 3 at 510 to complete the map of the baroreceptor region under the mapping electrodes 502 in zone 3 at 510.

Next, for mapping the baroreceptor region under the mapping electrodes 502 in zone 4 at 512, the controller 40 controls the switches 44 to connect one of the mapping electrodes 502 in zone 4 at 512 to the pulse generator 42 as a cathode and one or more of the mapping electrodes in zone 3 at 510 as an anode. The controller 40 controls the pulse generator 42 to provide bipolar stimulation to the baroreceptor region through the connected mapping electrodes 502. Alternatively, in some embodiments, the controller 40 and the pulse generator 42 provide unipolar stimulation to the one of the mapping electrodes 502 connected as a cathode.

The controller 40 receives the signals from the sensor 36 and analyzes the signals to obtain the physiological response from the patient, which is in response to stimulation of the baroreceptor region under the cathode connected mapping electrode. The controller 40 stores the data in the map of the baroreceptor region, indicating the cathode connected mapping electrode that was stimulated and the corresponding physiological response. This process can be repeated for each of the mapping electrodes in zone 4 at 512 to complete the map of the baroreceptor region under the mapping electrodes 502 in zone 4 at 512. In some embodiments, this process can be repeated for a select number of mapping electrodes, such as two or three mapping electrodes, in zone 4 at 512 to complete the map of the baroreceptor region under the mapping electrodes 502 in zone 4 at 512.

Next, the controller 40 analyzes the maps of the baroreceptor region to determine which zone of zone 3 at 510 and zone 4 at 512 is most likely to include the mapping electrode or mapping electrodes that, when stimulated, provide the effective physiological response. The zone that is most likely to include this mapping electrode is selected and the process continues. In some embodiments, the effective physiological response is the largest reduction in the blood pressure of the patient. In some embodiments, the effective physiological response is the largest reduction in the heart rate of the patient. In some embodiments, the effective physiological response is the largest change in the tissue impedance of the patient.

In some embodiments, the controller 40 displays the map of the baroreceptor region and, after viewing the map of the baroreceptor region, a user selects one of the two zones. In some embodiments, the controller 40 selects the zone that is most likely to include the mapping electrode or mapping electrodes that, when stimulated, provide the effective physiological response. In some embodiments, the controller 40 selects the zone by comparing the individual physiological response values in one zone to the individual physiological response values in the other zone and selecting the zone that has the largest physiological response value. In some embodiments, the controller 40 selects the zone by averaging the physiological response values in one zone and averaging the physiological response values in the other zone and selecting the zone that provides the largest average physiological response value. In some embodiments, the controller 40 selects the zone by summing the physiological response values in one zone and summing the physiological response values in the other zone and selecting the zone that provides the largest sum.

Figure 22:
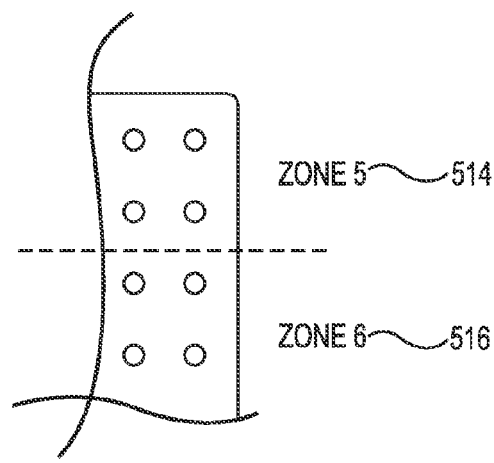
FIG. 22 is a diagram illustrating the selection of zone 4 and the division of zone 4 into a zone 5 and a zone 6, according to some embodiments described in the disclosure.

FIG. 22 is a diagram illustrating the selection of zone 4 at 512 and the division of zone 4 at 512 into a zone 5 at 514 and a zone 6 at 516 as indicated by the dashed line and according to some embodiments described in the disclosure. The zone 5 at 514 includes the mapping electrodes 502 in the upper half of zone 4 at 512 and the zone 6 at 516 includes the mapping electrodes 502 in the lower half of zone 4 at 512.

Next, the controller 40 controls the switches 44 and the pulse generator 42 and receives the signals from the sensor 36 and analyzes the signals, as described above, to map the baroreceptor regions under the mapping electrodes 502 in zone 5 at 514 and in zone 6 at 516. In some embodiments, the controller 40 selects a select number of mapping electrodes, such as two or three mapping electrodes, in zone 5 at 514 to complete the map of the baroreceptor region under the mapping electrodes 502 in zone 5 at 514, and a select number of mapping electrodes, such as two or three mapping electrodes, in zone 6 at 516 to complete the map of the baroreceptor region under the mapping electrodes 502 in zone 6 at 516.

In addition, the controller 40 analyzes the maps of the baroreceptor region to determine which zone of zone 5 at 514 and in zone 6 at 516 is most likely to include the mapping electrode or mapping electrodes that, when stimulated, provide the effective physiological response. The zone that is most likely to include this mapping electrode is selected and the process continues. In some embodiments, the effective physiological response is the largest reduction in the blood pressure of the patient. In some embodiments, the effective physiological response is the largest reduction in the heart rate of the patient. In some embodiments, the effective physiological response is the largest change in the tissue impedance of the patient.

In some embodiments, the controller 40 displays the map of the baroreceptor region and, after viewing the map of the baroreceptor region, a user selects one of the two zones. In some embodiments, the controller 40 selects the zone that is most likely to include the mapping electrode or mapping electrodes that, when stimulated, provide the effective physiological response. In some embodiments, the controller 40 selects the zone by comparing the individual physiological response values in one zone to the individual physiological response values in the other zone and selecting the zone that has the largest physiological response value. In some embodiments, the controller 40 selects the zone by averaging the physiological response values in one zone and averaging the physiological response values in the other zone and selecting the zone that provides the largest average physiological response value. In some embodiments, the controller 40 selects the zone by summing the physiological response values in one zone and summing the physiological response values in the other zone and selecting the zone that provides the largest sum.

Figure 23:
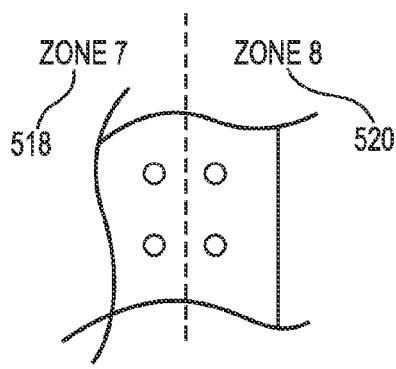
FIG. 23 is a diagram illustrating the selection of zone 6 and the division of zone 6 into a zone 7 and a zone 8, according to some embodiments described in the disclosure.

FIG. 23 is a diagram illustrating the selection of zone 6 at 516 and the division of zone 6 at 516 into a zone 7 at 518 and a zone 8 at 520 as indicated by the dashed line and according to some embodiments described in the disclosure. The zone 7 at 518 includes the mapping electrodes 502 in the left side of zone 6 at 516 and zone 8 at 520 includes the mapping electrodes 502 in the right side of zone 6 at 516.

Next, the controller 40 controls the switches 44 and the pulse generator 42 and receives the signals from the sensor 36 and analyzes the signals, as described above, to map the baroreceptor regions under the mapping electrodes 502 in zone 7 at 518 and at zone 8 at 520. In some embodiments, the controller 40 selects one mapping electrode in zone 7 at 518 to complete the map of the baroreceptor region under the mapping electrodes 502 in zone 7 at 518, and one mapping electrode in zone 8 at 520 to complete the map of the baroreceptor region under the mapping electrodes 502 in zone 8 at 520.

In addition, the controller 40 analyzes the maps of the baroreceptor region to determine which zone of zone 7 at 518 and zone 8 at 520 is most likely to include the mapping electrode that, when stimulated, provides the effective physiological response, which can be the larger or largest physiological response. The zone that is most likely to include this mapping electrode is selected and the process continues. In some embodiments, the effective physiological response is the largest reduction in the blood pressure of the patient. In some embodiments, the effective physiological response is the largest reduction in the heart rate of the patient. In some embodiments, the effective physiological response is the largest change in the tissue impedance of the patient.

In some embodiments, the controller 40 displays the map of the baroreceptor region and, after viewing the map of the baroreceptor region, a user selects one of the two zones. In some embodiments, the controller 40 selects the zone that is most likely to include the mapping electrode or mapping electrodes that, when stimulated, provide the effective physiological response. In some embodiments, the controller 40 selects the zone by comparing the individual physiological response values in one zone to the individual physiological response values in the other zone and selecting the zone that has the largest physiological response value. In some embodiments, the controller 40 selects the zone by averaging the physiological response values in one zone and averaging the physiological response values in the other zone and selecting the zone that provides the largest average physiological response value. In some embodiments, the controller 40 selects the zone by summing the physiological response values in one zone and summing the physiological response values in the other zone and selecting the zone that provides the largest sum.

Figure 24:
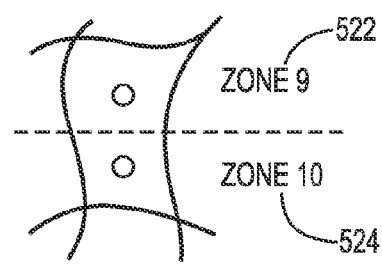
FIG. 24 is a diagram illustrating the selection of zone 7 and the division of zone 7 into a zone 9 and a zone 10, according to some embodiments described in the disclosure.

FIG. 24 is a diagram illustrating the selection of zone 7 at 518 and the division of zone 7 at 518 into a zone 9 at 522 and a zone 10 at 524 as indicated by the dashed line and according to some embodiments described in the disclosure. The zone 9 at 522 includes one mapping electrode 502 in the upper half of zone 7 at 518 and the zone 10 at 524 includes another mapping electrode 502 in the lower half of zone 7 at 518.

Next, the controller 40 controls the switches 44 and the pulse generator 42 and receives the signals from the sensor 36 and analyzes the signals, as described above, to map the baroreceptor region under the mapping electrodes 502 in zone 9 at 522 and zone 10 at 524. In addition, the controller 40 analyzes the maps of the baroreceptor region to determine which of the mapping electrodes in zone 9 at 522 and zone 10 at 524 is the mapping electrode that, when stimulated, provides the effective physiological response. This mapping electrode is selected and the marking and placement of the implantable device process continues. In some embodiments, the effective physiological response is the largest reduction in the blood pressure of the patient. In some embodiments, the effective physiological response is the largest reduction in the heart rate of the patient. In some embodiments, the effective physiological response is the largest change in the tissue impedance of the patient.

Figure 25:
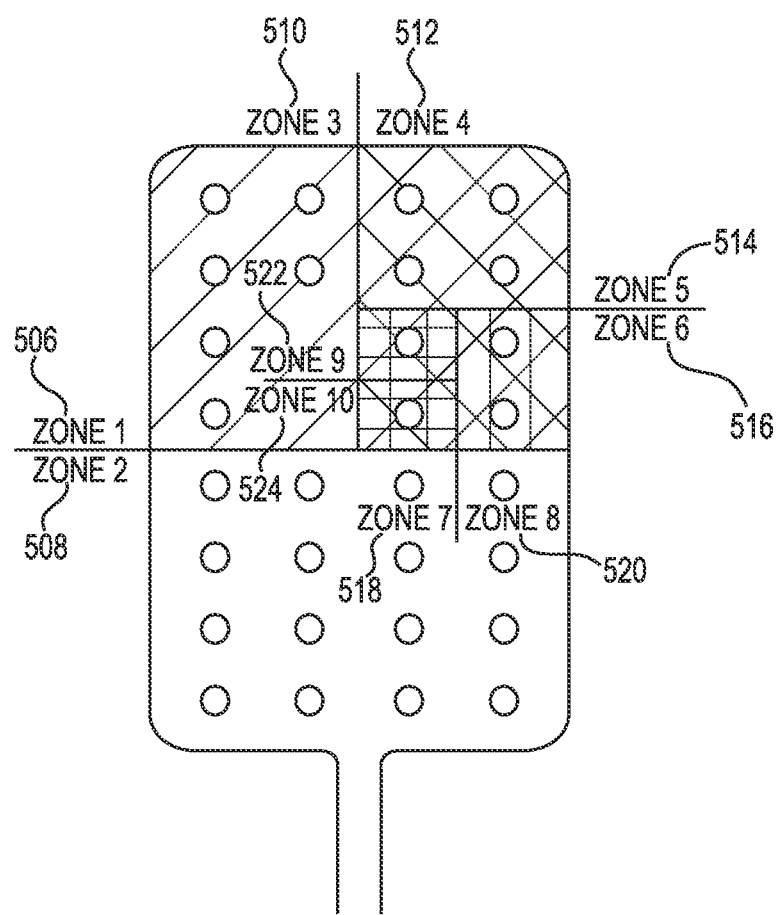
FIG. 25 is a diagram illustrating all of the zones 1-10 and indicating the selected zones with different cross-hatching for the refinement process of FIGS. 20-24, according to some embodiments described in the disclosure.

FIG. 25 is a diagram illustrating all of the zones 1-10 and indicating the selected zones with different cross-hatching for the refinement process of FIGS. 20-24, according to some embodiments described in the disclosure. The zone 1 at 506 was selected over the zone 2 at 508, and the zone 4 at 512 was selected over the zone 3 at 510. Also, the zone 6 at 516 was selected over the zone 5 at 514, and the zone 7 at 518 was selected over the zone 8 at 520. To refine it down to one mapping electrode, either zone 9 at 522 or zone 10 at 524 is selected.

In some embodiments, the mapping process described above with reference to FIGS. 20-25 can be interrupted at any point in the process and the user can stimulate and/or select mapping electrodes 502 as desired by the user.

In one example, the controller 40 controls the pulse generator 42 to stimulate selected mapping electrodes 502. The controller 40 receives signals from the sensor 36, which indicate the blood pressure of the patient, and the controller 40 analyzes the signals to obtain the reductions in the blood pressure of the patient. The controller 40 stores the data in a map of the baroreceptor region, indicating the cathode electrode stimulated and the corresponding reduction in the blood pressure. The controller 40 determines a first average of the reductions in the blood pressure in one zone and a second average of the reductions in the blood pressure in the other zone. The controller 40 selects the zone with the largest or highest average reduction in blood pressure.

In one example, the controller 40 controls the pulse generator 42 to stimulate connected mapping electrodes 502. The controller 40 receives signals from the sensor 36, which indicate the heart rate of the patient, and the controller 40 analyzes the signals to obtain the reductions in the heart rate of the patient. The controller 40 stores the data in a map of the baroreceptor region, indicating the cathode electrode stimulated and the corresponding reduction in the heart rate. The controller 40 determines a first average of the reductions in the heart rate in one zone and a second average of the reductions in the heart rate in the other zone. The controller 40 selects the zone with the largest or highest average reduction in heart rate.

In one example, the controller 40 controls the pulse generator 42 to stimulate connected mapping electrodes 502. The controller 40 receives signals from the sensor 36, which indicate the blood pressure of the patient, and the controller 40 analyzes the signals to obtain the reductions in the blood pressure of the patient. The controller 40 stores the data in a map of the baroreceptor region, indicating the cathode electrode stimulated and the corresponding reduction in the blood pressure. The controller 40 determines a first average of the reductions in the blood pressure in one zone and a second average of the reductions in the blood pressure in the other zone. A user selects the zone with the largest or highest average reduction in blood pressure.

In one example, the controller 40 controls the pulse generator 42 to stimulate connected mapping electrodes 502. The controller 40 receives signals from the sensor 36, which indicate the heart rate of the patient, and the controller 40 analyzes the signals to obtain the reductions in the heart rate of the patient. The controller 40 stores the data in a map of the baroreceptor region, indicating the cathode electrode stimulated and the corresponding reduction in the heart rate. The controller 40 determines a first average of the reductions in the heart rate in one zone and a second average of the reductions in the heart rate in the other zone. A user selects the zone with the largest or highest average reduction in heart rate.

In one example, the controller 40 controls the pulse generator 42 to stimulate connected mapping electrodes 502. The controller 40 receives signals from the sensor 36, which indicate the blood pressure of the patient, and the controller 40 analyzes the signals to obtain the reductions in the blood pressure of the patient. The controller 40 stores the data in a map of the baroreceptor region, indicating the cathode electrode stimulated and the corresponding reduction in the blood pressure. The controller 40 compares the reductions in the blood pressure in one zone to the reductions in the blood pressure in the other zone and selects the zone including the largest or highest reduction in blood pressure.

In one example, the controller 40 controls the pulse generator 42 to stimulate connected mapping electrodes 502. The controller 40 receives signals from the sensor 36, which indicate the heart rate of the patient, and the controller 40 analyzes the signals to obtain the reductions in the heart rate of the patient. The controller 40 stores the data in a map of the baroreceptor region, indicating the cathode electrode stimulated and the corresponding reduction in the heart rate. The controller 40 compares the reductions in the heart rate in one zone to the reductions in the heart rate in the other zone and selects the zone including the largest or highest reduction in heart rate.

In one example, the controller 40 controls the pulse generator 42 to stimulate connected mapping electrodes 502. The controller 40 receives signals from the sensor 36, which indicate the blood pressure of the patient, and the controller 40 analyzes the signals to obtain the reductions in the blood pressure of the patient. The controller 40 stores the data in a map of the baroreceptor region, indicating the cathode electrode stimulated and the corresponding reduction in the blood pressure. A user compares the reductions in the blood pressure in one zone to the reductions in the blood pressure in the other zone and selects the zone including the largest or highest reduction in blood pressure.

In one example, the controller 40 controls the pulse generator 42 to stimulate connected mapping electrodes 502. The controller 40 receives signals from the sensor 36, which indicate the heart rate of the patient, and the controller 40 analyzes the signals to obtain the reductions in the heart rate of the patient. The controller 40 stores the data in a map of the baroreceptor region, indicating the cathode electrode stimulated and the corresponding reduction in the heart rate. A user compares the reductions in the heart rate in one zone to the reductions in the heart rate in the other zone and selects the zone including the largest or highest reduction in heart rate.

Figure 26A:
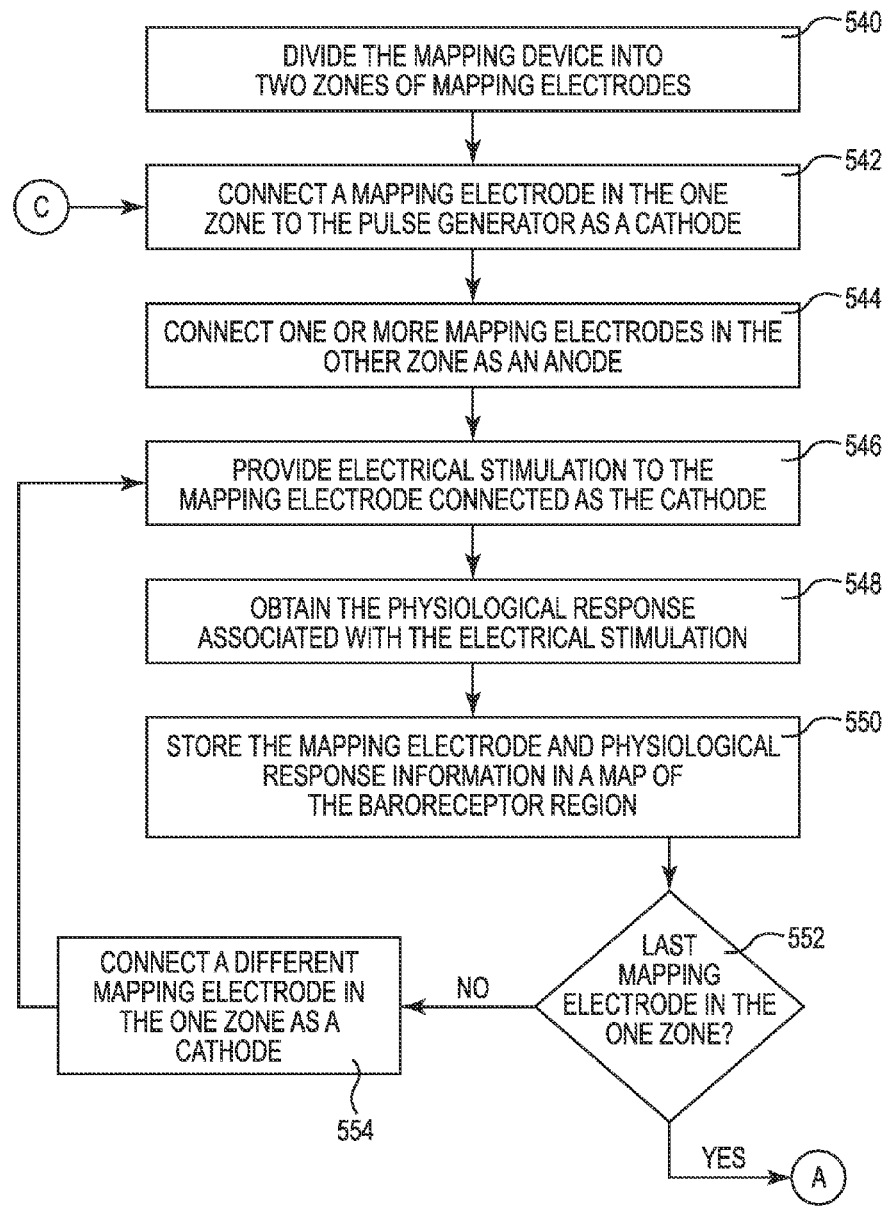
FIG. 26A is a flowchart diagram illustrating a first part of a mapping algorithm for mapping a baroreceptor region, according to some embodiments described in the disclosure.
Figure 26B:
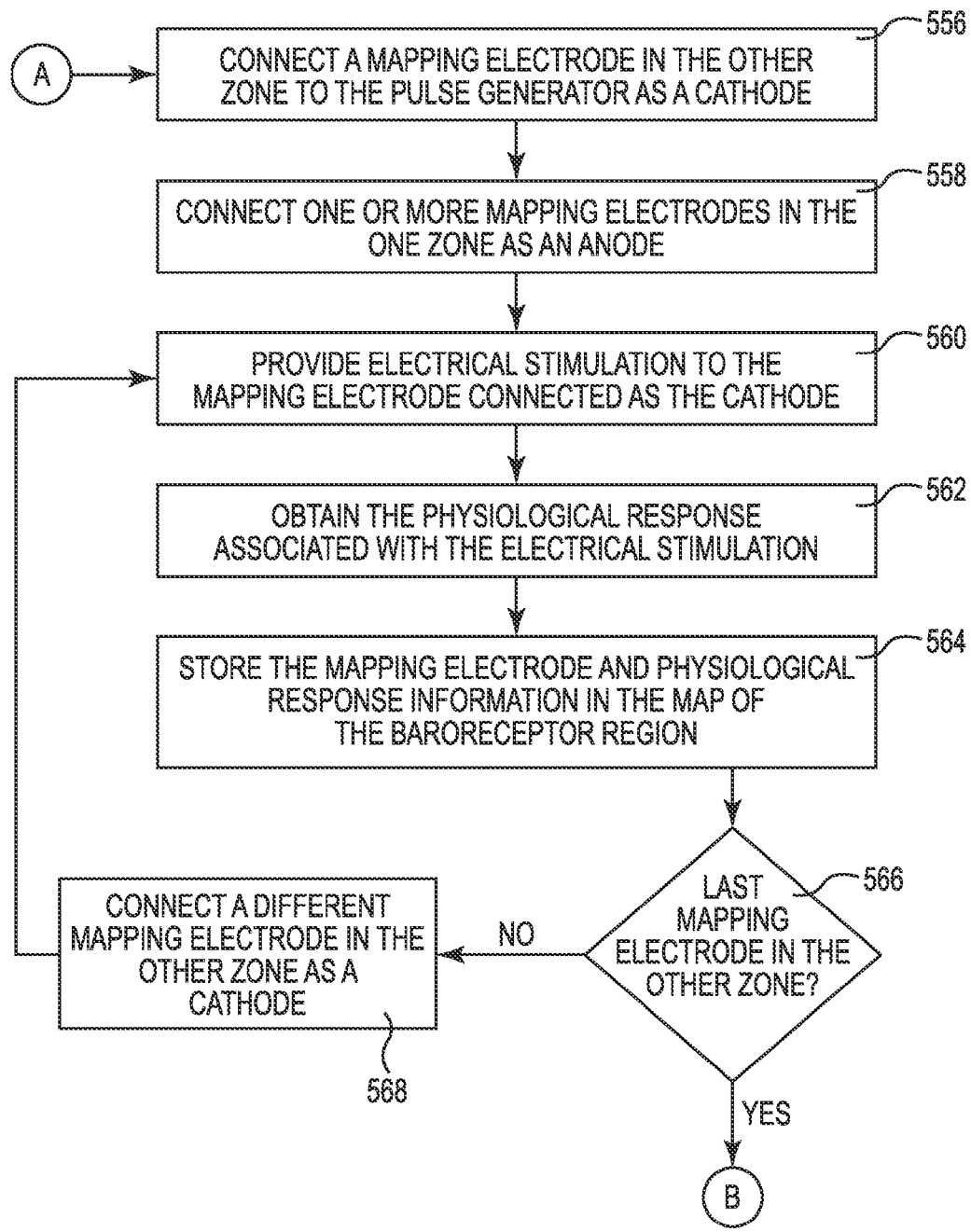
FIG. 26B is a flowchart diagram illustrating a second part of the mapping algorithm for mapping the baroreceptor region, according to some embodiments described in the disclosure.
Figure 26C:
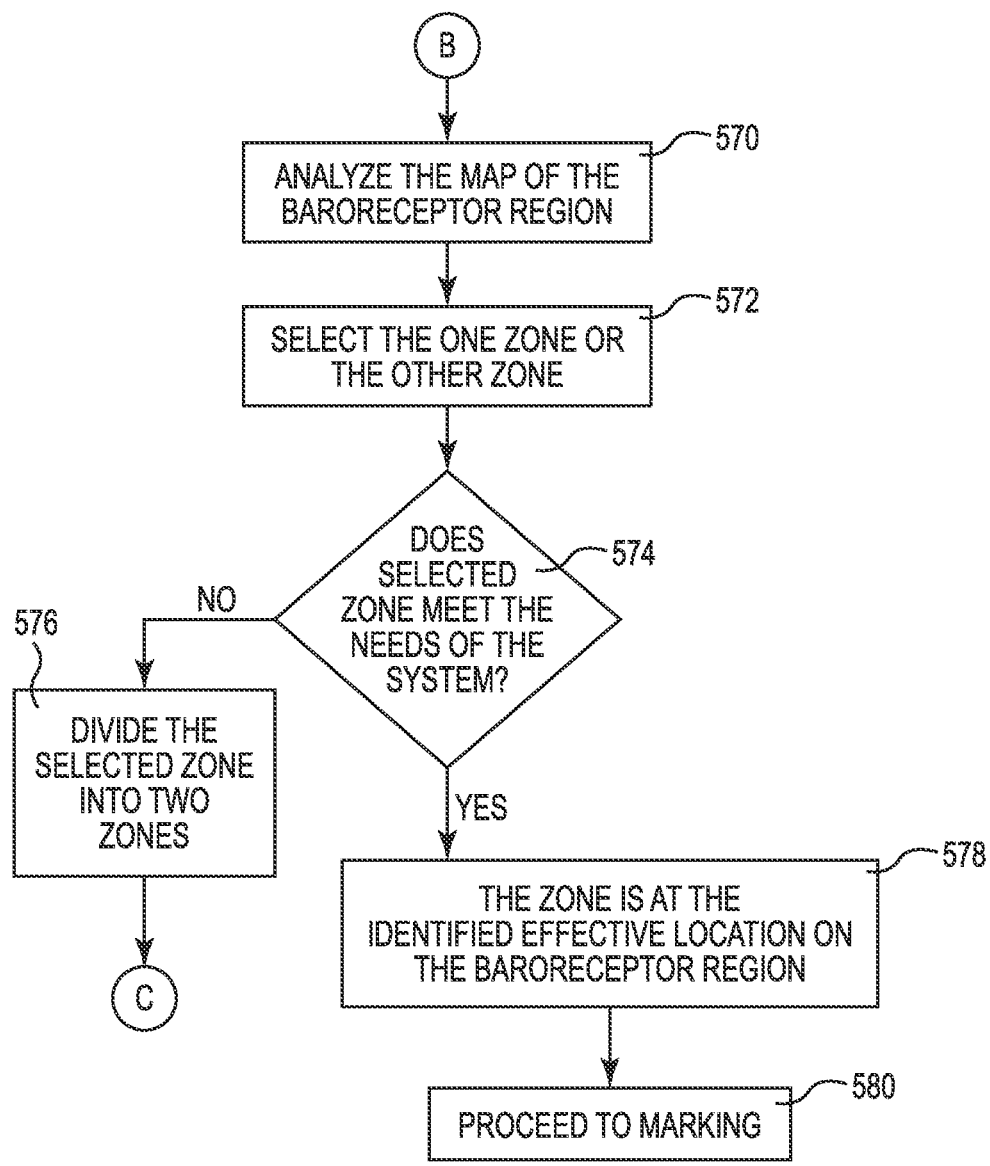
FIG. 26C is a flowchart diagram illustrating a third part of the mapping algorithm for mapping the baroreceptor region, according to some embodiments described in the disclosure.

FIGS. 26A-26C are flowchart diagrams illustrating a mapping algorithm for mapping a baroreceptor region, according to some embodiments described in the disclosure. The mapping device, such as one of the mapping devices 22, 100, 120, 130, 150, and 404, is placed on a patient for mapping the baroreceptor region of the patient. A stimulator, such as stimulator 24, provides the mapping algorithm.

At 540, the stimulator divides the mapping device into two zones of mapping electrodes. At 542, the stimulator connects one of the mapping electrodes in one zone to a pulse generator, such as the pulse generator 42, as a cathode and, at 544, the stimulator connects one or more of the mapping electrodes in the other zone to the pulse generator as an anode. The stimulator can connect any one of the mapping electrodes in the other zone or any combination of the mapping electrodes in the other zone as an anode. In some embodiments, a surface patch is placed on the patient's skin and the stimulator connects the surface patch as an anode. In some embodiments, the stimulator connects an independent electrode that can be part of the mapping device or from a separate probe as an anode.

At 546, the stimulator controls the pulse generator to provide bipolar electrical stimulation to the baroreceptor region under the cathode connected mapping electrode through the cathode and anode connected mapping electrodes. Alternatively, in some embodiments, the stimulator controls the pulse generator to provide unipolar electrical stimulation to the baroreceptor region under the cathode connected mapping electrode using the cathode connected mapping electrode.

At 548, the physiological response associated with the electrical stimulation of the baroreceptor region under the cathode connected mapping electrode is obtained from the patient. This physiological response is obtained either manually by a user or automatically with the stimulator and an attached sensor. Also, at 550, the identity of the cathode connected mapping electrode and the associated physiological response information is stored in a map of the baroreceptor region, either manually by a user or automatically with the stimulator.

If one or more of the mapping electrodes in the one zone remain to be connected as a cathode at 552, the stimulator proceeds to connect a different one of the mapping electrodes in the one zone as a cathode at 554 and the process repeats itself through the steps of providing electrical stimulation at 546, obtaining the associated physiological response at 548, and storing the identity of the stimulated cathode connected mapping electrode and the associated physiological response at 550.

If all of the mapping electrodes or all of a selected number of the mapping electrodes in the one zone have been stimulated and mapped at 552, the stimulator proceeds to connect one of the mapping electrodes in the other zone to the pulse generator as a cathode at 556 and, at 558, the stimulator connects one or more of the mapping electrodes in the one zone (that was just mapped) to the pulse generator as an anode. The stimulator can connect any one of the mapping electrodes in the zone that was just mapped or any combination of the mapping electrodes in the zone that was just mapped as an anode. In some embodiments, the stimulator can connect a surface patch on the patient's skin as an anode. In some embodiments, the stimulator can connect an independent electrode that is part of the mapping device or from a separate probe as an anode.

At 560, the stimulator controls the pulse generator to provide bipolar electrical stimulation to the baroreceptor region under the cathode connected mapping electrode through the cathode and anode connected mapping electrodes. Alternatively, in some embodiments, the stimulator controls the pulse generator to provide unipolar electrical stimulation to the baroreceptor region under the cathode connected mapping electrode using the cathode connected mapping electrode.

At 562, the physiological response associated with the electrical stimulation of the baroreceptor region under the cathode connected mapping electrode is obtained from the patient either manually by a user or automatically with the stimulator and an attached sensor. Also, at 564, the identity of the cathode connected mapping electrode and the associated physiological response information is stored in a map of the baroreceptor region either manually by a user or automatically with the stimulator.

If one or more of the mapping electrodes in the other zone remain to be connected as a cathode at 566, the stimulator proceeds to connect a different one of the mapping electrodes in the other zone as a cathode at 568 and the process repeats itself through the steps of providing electrical stimulation at 560, obtaining the associated physiological response at 562, and storing the identity of the stimulated cathode connected mapping electrode and the associated physiological response at 564.

If all of the mapping electrodes or all of a selected number of the mapping electrodes in the other zone have been stimulated and mapped at 566, the process continues with analyzing the map of the baroreceptor region at 570 and selecting the one zone or the other zone as including the most likely location for long term stimulation of baroreceptors in the baroreceptor region at 572. In some embodiments, analyzing the map of the baroreceptor region at 570 can be done manually. In some embodiments, analyzing the map of the baroreceptor region at 570 can be done automatically with the stimulator.

In some embodiments, the permanently implantable device, such as each of the implantable devices 220, 240, 250, and 270, has an implantable device electrode that is larger than one of the mapping electrodes. In some embodiments, the permanently implantable device has an implantable device electrode that is as large as or larger than a combination of multiple mapping electrodes, such that the implantable device electrode covers the same area on the baroreceptor region as the multiple mapping electrodes. Where the implantable device electrode is larger than one of the mapping electrodes or covers the same area as multiple mapping electrodes, the final zone selected can include multiple mapping electrodes and meet the needs of the system.

If the selected zone includes more than the number of mapping electrodes for meeting the needs of the system at 574, the stimulator divides the selected zone into two zones at 576 and the process repeats itself from the step of connecting a mapping electrode in one zone to the pulse generator as a cathode at 542. In some embodiments, two or more physiological responses are obtained for mapping electrodes in a zone, as the zone is selected and the process repeats itself from the step of connecting a mapping electrode in one zone to the pulse generator as a cathode at 542.

If the selected zone includes the number of mapping electrodes or less than the number of mapping electrodes for meeting the needs of the system at 574, the location of the zone is a good candidate for the identified effective location of baroreceptors in the baroreceptor region, as indicated at 578. The process continues with marking the location at 580. In some embodiments, the mapping process described above with reference to FIGS. 26A-26C is part of the method of FIG. 13. In some embodiments, the mapping process described above with reference to FIGS. 26A-26C can be interrupted at any step in the process and the user can stimulate and/or select any one or more than one of the mapping electrodes as being at the identified effective location on the baroreceptor region.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A system for mapping and marking baroreceptors of a patient, comprising:
   a mapping device that includes a plurality of electrodes to be situated on the patient;
   a marker to be inserted through the mapping device and attached to the patient and to mark a location of at least one of the plurality of electrodes based on an analysis of patient physiological responses to stimulation of the plurality of electrodes; and
   a stimulator programmed to divide the plurality of electrodes into a first electrode zone having first electrodes and a second electrode zone having second electrodes and to stimulate electrodes in the first electrode zone and the second electrode zone to obtain first patient physiological responses, wherein one of the first electrode zone and the second electrode zone is selected based on the first patient physiological responses.

2. The system of claim 1, wherein the stimulator is to divide the selected one of the first electrode zone and the second electrode zone into a third electrode zone and a fourth electrode zone and to stimulate electrodes in the third electrode zone and the fourth electrode zone to obtain second patient physiological responses, wherein one of the third electrode zone and the fourth electrode zone is selected based on the second patient physiological responses.

3. The system of claim 2, wherein the stimulator is to divide the selected one of the third electrode zone and the fourth electrode zone into a fifth electrode zone and a sixth electrode zone and to stimulate electrodes in the fifth electrode zone and the sixth electrode zone to obtain third patient physiological responses, wherein one of the fifth electrode zone and the sixth electrode zone is selected based on the third patient physiological responses.

4. The system of claim 1, wherein the stimulator selects the at least one of the plurality of electrodes to be marked by the marker.

5. The system of claim 1, wherein a user selects the at least one of the plurality of electrodes to be marked by the marker.

6. The system of claim 1, wherein the stimulator is to select at least one cathode electrode in the first electrode zone and at least one anode electrode in the second electrode zone and provide bipolar stimulation to the selected electrodes to obtain the first patient physiological responses.

7. The system of claim 6, wherein the stimulator switches to selecting the at least one cathode electrode in the second electrode zone and the at least one anode electrode in the first electrode zone and provides bipolar stimulation to the selected electrodes to obtain the first patient physiological responses.

8. The system of claim 1, wherein the stimulator selects the one of the first electrode zone and the second electrode zone based on the first patient physiological responses.

9. The system of claim 1, comprising a sensor to sense the patient physiological responses and provide signals that indicate the patient physiological responses, wherein the stimulator receives the signals and analyzes the signals to determine the first patient physiological responses.

* * * * *